United States Patent
Hodges et al.

(10) Patent No.: US 8,637,678 B2
(45) Date of Patent: Jan. 28, 2014

(54) METHODS FOR THE PREPARATION OF ARYL AMIDES

(75) Inventors: George Robert Hodges, Bracknell (GB); Lisa Mitchell, Bracknell (GB); Alan James Robinson, Bracknell (GB)

(73) Assignee: Syngenta Limited, Guildford, Surrey (GB)

(*) Notice: Subject to any disclaimer, the term of this patent is extended or adjusted under 35 U.S.C. 154(b) by 0 days.

(21) Appl. No.: 13/142,110

(22) PCT Filed: Dec. 16, 2009

(86) PCT No.: PCT/EP2009/067286
§ 371 (c)(1),
(2), (4) Date: Jun. 24, 2011

(87) PCT Pub. No.: WO2010/072632
PCT Pub. Date: Jul. 1, 2010

(65) Prior Publication Data
US 2011/0263869 A1 Oct. 27, 2011

Related U.S. Application Data

(60) Provisional application No. 61/140,650, filed on Dec. 24, 2008.

(30) Foreign Application Priority Data

Jun. 19, 2009 (EP) .................... 09163256

(51) Int. Cl.
| C07D 231/10 | (2006.01) |
| C07C 22/04 | (2006.01) |
| C07C 49/12 | (2006.01) |
| C07C 43/30 | (2006.01) |
| C07C 241/00 | (2006.01) |
| C07D 333/02 | (2006.01) |

(52) U.S. Cl.
USPC ........ 548/374.1; 570/182; 570/183; 568/373; 568/592; 564/251; 549/81

(58) Field of Classification Search
USPC ........ 548/374.1; 570/182, 183; 568/373, 592; 564/251; 549/81
See application file for complete search history.

(56) References Cited

U.S. PATENT DOCUMENTS

| 2003/0065187 A1 | 4/2003 | Buchwald et al. |
| 2006/0264460 A1 | 11/2006 | Green et al. |
| 2007/0259846 A1 | 11/2007 | Hoenke et al. |

FOREIGN PATENT DOCUMENTS

| EP | 1932836 | 6/2008 |
| WO | 03101966 | 12/2003 |
| WO | WO 2005/026149 * | 3/2005 |
| WO | 2007057140 | 5/2007 |
| WO | WO 2007057140 * | 5/2007 |
| WO | 2007109362 | 9/2007 |
| WO | WO 2007146758 * | 12/2007 |
| WO | 2008000922 | 1/2008 |
| WO | 2008016192 | 2/2008 |
| WO | 2008058341 | 5/2008 |

OTHER PUBLICATIONS

Siffert, H.L. Tidahy S. Catalytic activity of copper and palladium based catalysts for toluene total oxidation. Catalysis Today. 119 (2007) 317-320.*
Kang S-K et al: "Copper-Catalyzed N-Arylation of Aryl Iodides With Benzamides or Nitrogen Heterocylces in the Presence of Ethylenediamine" Synlett, Georg Thieme Verlag, DE, vol. 3, Mar. 4, 2002, pp. 427-430.
LV, X.; Bao, W.: "A B-ketoester as novel, efficient and versatile ligand for Copper(I)-Catalyzed C-N, C-O and C-S coupling reactions", Journal of Organic Chemistry, vol. 72, 2007, pp. 3863-3867.
Hosseinzadeh, R.; Tajbakhsh. M.; Mohadjerani, M.; Mehdinejad, H.: "Copper-Catalyzed amidation of aryl iodides using KF/A1203: An improved protocol" Synlett, vol. 9, 2004, pp. 1517-1520.
Hosseinzadeh Rahman et al: "Copper-Catalyzed Amidation of Aryl Iodides in the Presence of Various Chelating Ligands", Journal of the Chinese Chemical Society, Chinese Electronic Periodical Services, China, vol. 55, No. 3, Jun. 1, 2008, pp. 649-653.
Wei Deng et al: "Amino acid mediated Goldberg reactions between amides and aryl iodides", Tetrahedron Letters, Elsevier, Amsterdam, NL, vol. 45, Jan. 1, 2004, pp. 2311-2315.
Mino Takashi et al: "Copper-Catalyzed N-Arylation of Amides and Azoles Using Phosphine-Free Hydrazone Ligands" Synlett, Georg Thieme Verlag, DE, No. 4, Jan. 1, 2008, pp. 614-620.

(Continued)

*Primary Examiner* — Samantha Shterengarts
(74) *Attorney, Agent, or Firm* — R. Kody Jones

(57) ABSTRACT

The present invention relates to methods of initiating a reaction represented by scheme (1), wherein Q is optionally substituted aryl or optionally substituted heteroaryl; X is halogen or a sulphonate; P is an organic radical; R is hydrogen or an organic radical; wherein the catalyst comprises copper and a ligand; comprising providing the compound of formula III in liquid form prior to contacting the compound of formula III with the catalyst.

Scheme 1

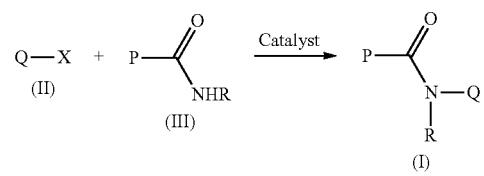

16 Claims, 1 Drawing Sheet

(56) References Cited

OTHER PUBLICATIONS

Figure 1:
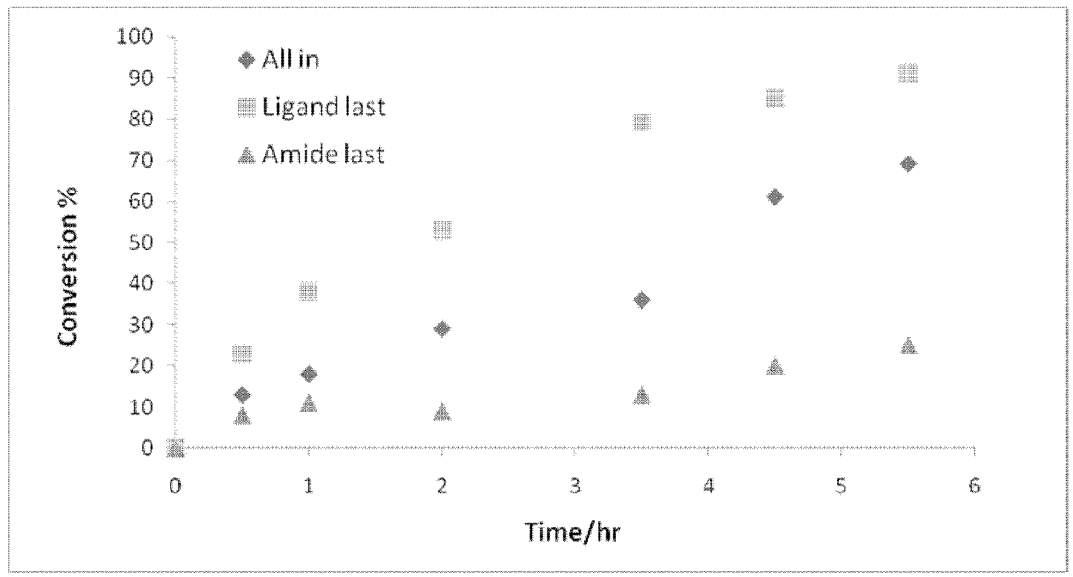

Heng, C.M.; Xuan, Z.J.: "Oxazolidin-2-one-promoted CuI-catalyzed amidation of aryl halides and cyclization of o-halobenzanilidesnes", Synlett, vol. 9, May 7, 2008, pp. 1335-1340.

Artis Klapars et al: "A General and Efficient Copper Catalyst for the Amidation of Aryl Halides and the N-Arylation of Nitrogen Heterocycles", Journal of the American Chemical Society, American Chemical Society, New York, USA, vol. 123, Dec. 7, 2001, pp. 7727-7729.

Klapars, A et al: "A General and Efficient Copper Catalyst for the Amidation of Aryl Halides", Journal of the American Chemical Society, American Chemical Society, New York, USA, vol. 124, Jan. 1, 2002, pp. 7421-7428.

Tubaro C et al: "Efficient catalysis of Ullmann-type arylation reactions by a novel trinuclear copper(I) complex with a chelating tricarbene ligand", Tetrahedron Elsevier Science Publishers, Amsterdam, NL, vol. 64, No. 19, May 5, 2008, pp. 4187-4195.

Chen, W.; Li, J.; Fang, D.; Feng, C.; Zhang, C.: "Copper-catalyzed one-pot multicomponent coupling reaction of phenols, amides and 4-bromophenyl iodide", Organic Letters, vol. 10, No. 20, Sep. 25, 2008, pp. 4565-4568.

Cristau H-J et al: "Highly Efficient and Mild Copper-Catalyzed N- and C-Arylations with Aryl Bromides and Iodides" Chemistry—A European Journal, Wiley—V C H Verlag GMBH & CO, KGAA, Weinheim, DE, vol. 10, Nov. 19, 2004, pp. 5607-5622.

Chansekhar, S.; Sultana, S.S.; Yaragorla, S.R.; Reddy, N.R.;: "Copper-catalyzed N-arylation of amines/amides in poly(ethylene glycol) as recyclable solvent medium", Synthesis, No. 5, 2006, pp. 839-842.

Zheng, N.; Buchwald, S.L.: "Copper-catalyzed regiospecific synthesis of N-alkylbenzimidazoles", Organic Letters, vol. 9, No. 23, 2007, pp. 4749-4752.

Hu et al: "Inhibition of Tpl2 kinase and TNFalpha production with quinoline-3-carbonitriles for the treatment of rheumatoid arthritis", Bioorganic & Medicinal Chemistry Letters, Pergamon, Elsevier Science, GB, vol. 16, No. 23, Nov. 7, 2006, pp. 6067-6072.

Ibrahim, N.; Legraverend, M.: Synthesis of 6,7,8-trisubstittued purines via a copper-catalyzed amidation reaction, Journal of Organic Chemistry, vol. 74, Nov. 14, 2008, pp. 463-465.

Toto et al: "Synthesis of N-(iodophenyl)-amides via an unprecedented Ullman-Finkelstein tandem reaction", Tetrahedron Letters, Elsevier, Amsterdam, NL, vol. 47, No. 7, Feb. 13, 2006, pp. 1181-1186.

Tao et al: "Copper-catalyzed synthesis of primary arylamines from aryl halides and 2,2,2-trifluoroacetamide", Tetrahedron Letters, Elsevier, Amsterdam, NL, vol. 49, No. 1, Nov. 6, 2007, pp. 70-75.

Wiedemann, S.H.; Ellma, J.A.; Bergman, R.G.: "Rhodium-catalyzed direct C-H addition of 3,4-Dihydroquinazolines to Alkenes and their use in the total synthesis of Vasicoline", Journal of Organic Chemistry, vol. 71, 2006, pp. 1969-1976.

* cited by examiner

METHODS FOR THE PREPARATION OF ARYL AMIDES

This application is a 371 of International Application No. PCT/EP2009/067286 filed Dec. 16, 2009, which claims priority to 61/140,650 filed Dec. 24, 2008, and EP 09163256.2 filed Jun. 19, 2009, the contents of which are incorporated herein by reference.

The present invention relates to the preparation of aryl amides, more specifically to methods of forming aryl carbon-amide nitrogen bonds using copper based catalysts.

Fungicides for crop protection are generally produced in large quantities, e.g. in thousands of tons per year. Given the scale on which fungicides are produced any improvement to the production process can represent significant cost savings.

A number of fungicides have a chemical structure in which an amide nitrogen is attached to an aryl group. These include for example Isopyrazam, Sedaxane, Bixafen, Penthiopyrad and others. Generally, such aryl carbon-amide nitrogen chemical bonds may be formed by coupling the corresponding acyl chloride and aryl amine. For example, WO 04/035589 discloses Isopyrazam and describes a process in which pyrazolyl-4-carboxylic acid benzonorbornen-5-yl-amides are prepared by coupling the corresponding acyl chloride and amine. However, acyl chlorides are very sensitive to water and this can create technical issues when operating the reactions on a commercial scale.

WO 2008/006575 describes coupling amides and aryl halides using a copper based catalyst. This type of reaction involving formation of aryl-nitrogen bonds using a catalyst comprising copper and a ligand is described generally in WO 02/085838. However, we have found that following the described procedures does not always result in a procedure that is suitable for operating on a commercial scale. In particular, often the reaction proceeds too slowly and/or yields are too low.

We have investigated why the described procedures for coupling amides with aryl halides using copper based catalysts are not always optimal and have found, surprisingly, that the success of these reactions can depend on the availability of the amide for complexing with the catalyst when the reaction is initiated. In particular, we have found that the reaction can proceed more effectively if, prior to mixing, the amide is provided in a form such that it is available for complexing with the catalyst, e.g. by being provided in liquid form. Without being bound by theory it is thought that the amide stabilises the catalyst and that in the absence of amide the catalyst can denature.

Accordingly, in a first aspect of the invention there is provided a method of initiating a reaction represented by scheme 1:

Scheme 1

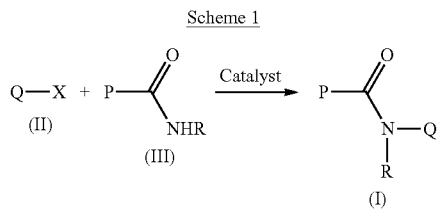

wherein
Q is optionally substituted aryl or optionally substituted heteroaryl;
X is halogen or a sulphonate;
P is an organic radical; preferably optionally substituted aryl or optionally substituted heteroaryl;
R is hydrogen or an organic radical;
wherein the catalyst comprises copper and a ligand;
comprising
providing the compound of formula III in liquid form prior to contacting the compound of formula III with the catalyst.

The compound of formula III is in liquid form, for example, when dissolved in solvent or when melted.

We have also found that performing the reaction in an organic polar solvent can surprisingly improve reaction efficiency. This is in contrast to the procedure described in the Example of WO 2008/006575 which describes using toluene. In fungicidal compounds group P shown in scheme 1 above is generally a heteroaryl group and, according to our investigations, it appears that when group P is heteroaryl the amide can be significantly less soluble than when group P is phenyl, for example. Without being bound by theory, we believe that using a polar solvent may speed up the availability of amide for complexing with the catalyst by allowing the amide to dissolve faster. Thus, it is believed that use of a polar solvent reduces the possibility of the catalyst becoming denatured.

Accordingly, in a further aspect of the invention, there is provided a method of preparing a compound of formula IA comprising performing the reaction represented by scheme 1A:

Scheme 1A

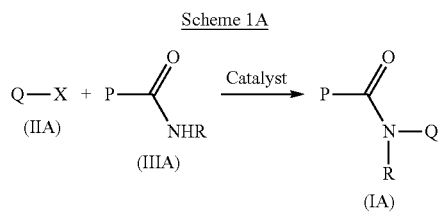

wherein
Q is optionally substituted aryl or optionally substituted heteroaryl;
X is halogen or a sulphonate;
P is optionally substituted aryl or optionally substituted heteroaryl, preferably optionally substituted heteroaryl;
R is hydrogen or an organic radical;
wherein the catalyst comprises copper and a ligand; and
wherein the reaction is performed in an organic polar solvent.

The organic polar solvent may be the compound of formula IIA.

Preferably the compound of formula III is a compound of formula XXII or LXIII

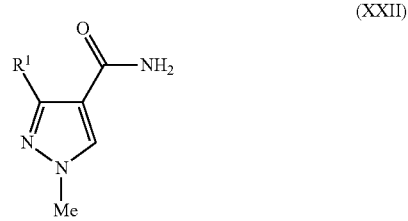

wherein $R^1$ is $C_1$-$C_4$-haloalkyl, preferably $C_1$-$C_4$-fluoroalkyl. For example, $R^1$ may be $CF_3$, $CHF_2$ or $CH_2F$, in particular $CHF_2$;

(LXIII)

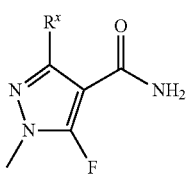

wherein R$^x$ is selected from CF$_3$, CHF$_2$ and CH$_3$.

It will be clear that compounds of formula IA, IIA and IIIA are compounds of formula I, II and III respectively, and that any reference herein to a compound of formula I, II or III, e.g. with regard to preferred substituent definitions and reaction conditions, also applies to compounds of formula IA, IIA and IIIA respectively, and vice versa. Likewise, any reference to compounds of formula I, II, III also applies to compounds of formula IB, IC, ID, IE, IF, IIB, IIC, IID, IIE, IIF and IIIB, IIIC, IIID, IIIE and IIIF respectively, and vice versa.

We have also had success in applying the discovery to reactions involving coupling amides to aryl chlorides. Aryl-Cl bonds are much less reactive compared to the corresponding aryl-Br or aryl-I bonds; indeed, it is recognised in the art that the high stability of aromatic carbon-chlorine bonds makes aryl chlorides very difficult to utilise (Grushin and Alper, Chem. Rev., 1994, 1047-1062). Without being bound by theory, it is thought that the higher reactivity of bromine or iodine substituted aryls may allow these reagents to assist in stabilising the catalyst, which assistance is much reduced or absent when chlorine substituted aryl compounds are used due to the inert nature of the aryl-Cl bond. Preferably X is Cl.

We have found that these coupling reactions, when performed according to the invention, proceed efficiently even when using aryl halides carrying an ortho substituent. In light of the proposed mechanism involving coordination of reactants around the metal ion it would reasonably be expected that ortho substituted aryls would require a greater amount of coordination space, thereby reducing the efficiency with which the reagent may complex to the copper. Indeed, the art recognises that steric hindrance influences the outcome of this type of reaction, e.g. in WO 02/085838.

Without being bound by theory, any contribution to stabilisation of the catalyst from the aryl halide would be expected to be reduced when Q is substituted at the ortho position with respect to X. Preferably Q is substituted at the ortho position with respect to X.

Furthermore, as far as we are aware there are no reports in the literature of reactions involving coupling amides with aryl chlorides using copper based catalysts in which the aryl is further substituted at the ortho position with respect to the chlorine substituent.

In a further aspect there is provided a method of preparing a compound of formula IB comprising performing the reaction represented by scheme 1B:

Scheme 1B

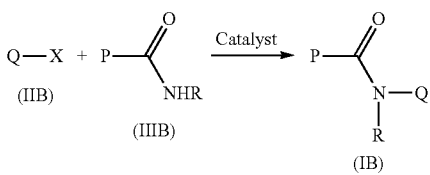

wherein
Q is aryl or heteroaryl, each carrying a substituent at the ortho position with respect to X, and wherein the aryl or heteroaryl may carry additional optional substituents;

X is Cl;
P is an organic radical;
R is hydrogen or an organic radical; and
wherein the catalyst comprises copper and a ligand.

In the methods of the invention the compound of formula III may be combined with the catalyst components in any order. For example, contacting the compound of formula III with the catalyst may involve contacting the compound of formula III with a mixture of copper and ligand, contacting the ligand with a mixture of compound of formula III and copper, or contacting copper with a mixture of compound of formula III and ligand. For the avoidance of doubt, "contacting component X with component Y" includes both "contacting X with Y" and "contacting Y with X".

The invention may comprise adding the copper to the ligand, or vice versa, in the presence of the compound of formula III. The method may comprise combining the copper with the ligand, or vice versa, to form a copper-ligand complex in the presence of the compound of formula III. Without being bound by theory it is thought that the catalyst is a copper-ligand complex.

Preferably, the invention comprises contacting the compound of formula III with the catalyst such that the catalyst substantially remains active, e.g. at least 50, 60, 70, 80, 90, 95, 96, 97, 98, 99 or 100% of the catalyst remains active.

The methods of the invention may comprise initiating the reaction by contacting the copper with the ligand in the presence of the compound of formula III, the compound of formula III being present in liquid form when the copper is contacted with the ligand. For example, the invention may comprise bringing the copper into contact with the ligand in the presence of the compound of formula III, e.g. to form the catalyst, wherein the compound of formula III is provided such that it is capable of forming a complex with the copper and/or catalyst, e.g. when the copper is brought into contact with the ligand to form the catalyst. Prior to performing the step of bringing the copper into contact with the ligand the copper and ligand will be separate, i.e. not in contact. The invention may comprise complexing the compound of formula III with the catalyst at a rate such that deactivation of the catalyst is reduced compared to deactivation of the catalyst in the absence of the compound of formula III.

The period during which the reaction is initiated, for example, includes the period prior to the formation of the compound of formula I during which the reagents and catalyst are combined.

In some cases it may be convenient to combine the copper and ligand before adding these to the compound of formula III. Although our results indicate that the catalyst is unstable in the absence of amide, loss of catalyst activity can be minimised by mixing the copper and ligand at lower temperatures, e.g. at ambient temperature. or if mixing occurs at higher temperature, minimising the time between combining the copper and ligand and adding to the compound of formula III. Preferably the catalyst is not heated in the absence of the compound of formula III.

For example, the invention may comprise the steps:
a) providing the compound of formula III in liquid form,
b) contacting the copper with the compound of formula III,
c) contacting the ligand with the compound of formula III, wherein step b) or step c) may be performed prior to step a), but preferably at least one of steps b) and c) is performed after step a). Step a) may comprise contacting, e.g. dissolving the compound of formula III, in solvent. This may or may not result in all the compound of formula III used being dissolved in the solvent. Providing at least some compound of formula III is dissolved in solvent the compound of formula III will then be available for complexing with the catalyst. Preferably, at least 0.5, 0.7, 1.0, 1.5, 2, 3, 4, or even 5 molar equivalents of compound of formula III are dissolved, relative to the amount of copper, prior to contact of the compound of formula III with the catalyst. More preferably at least one molar equivalent of compound of formula III is dissolved relative to the amount of copper.

Step a) may comprise heating the compound of formula III. Preferably the compound of formula III is heated to at least 40, 50, 60, 70, 80, 90, 100, 105, or even at least 110° C. in step a) e.g. prior to contacting the compound of formula III with both the copper and the ligand.

The reaction may be performed in a solvent, preferably an organic polar solvent. The compound of formula II and/or the ligand may serve as the solvent, or the solvent may be a different component. In some cases, the compound of formula III may serve as the solvent.

The method may comprise contacting the compound of formula III with solvent, e.g. the compound of formula II, and heating prior to contacting both of the ligand and the copper with the solvent. Heating may facilitate solvation of the compound of formula III, thereby allowing more compound of formula III to be available for complexing with the catalyst. Preferably the solvent and compound of formula III is heated to at least 40, 50, 60, 70, 80, 90, 100, 110, 120, 130, or even at least 140° C., e.g. 50-200° C., 80 to 180° C. 100-170° C., 130-160° C.° C. in step a) e.g. prior to contacting both of the copper and ligand in the solvent. The solvent and compound of formula III may be heated at any of the foregoing temperatures for any desired length of time, e.g. 1 second to 24 hours, e.g. 1-1000 minutes, e.g. 10 to 500 minutes, e.g. 30 to 300 minutes. The solvent and compound of formula III may be heated at any of the foregoing temperatures for at least 1, 10, 30, 60, or even at least 200 minutes. Preferably, the solvent with compound of formula III dissolved therein is heated at least at 100° C. for at least 100 minutes before the copper and ligand are both contacted with the solvent.

When the solvent is the compound of formula II, the method may include the additional step of melting the compound of formula II prior to contacting with the compound of formula III.

The compound of formula II may be combined with the other reagents at any stage.

Preferably, the compound of formula III is one which is a solid at 25° C. and atmospheric pressure.

The following preferred substituent definitions apply to all aspects of the invention and may be combined in any combination.

P may be alkyl, alkenyl, alkynyl, cycloalkyl, cycloalkyl-alkyl, aryl or heteroaryl; each of the foregoing may be optionally substituted.

P may be $C_1$-$C_4$-alkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl, phenyl, phenyl-$C_1$-$C_4$-alkyl heteroaryl or heteroaryl-$C_1$-$C_4$-alkyl, e.g. the term heteroaryl as defined below; each of the foregoing may be optionally substituted with $C_1$-$C_4$-alkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl, phenyl, phenyl-$C_1$-$C_4$-alkyl, $C_1$-$C_4$-alkoxy, $C_2$-$C_4$-alkenyloxy, $C_2$-$C_4$-alkynyloxy, $C_1$-$C_4$-alkoxy-$C_1$-$C_4$-alkyl, $C_1$-$C_4$-alkylthio, $C_1$-$C_4$-alkylsulfonyl, $C_1$-$C_4$-alkanoyl, hydroxyl, halogen (preferably fluorine), cyano, nitro, amino, $C_1$-$C_4$-alkylamino, $C_1$-$C_4$-dialkylamino, $C_1$-$C_4$-carbonyl, $C_1$-$C_4$-alkoxycarbonyl, $C_2$-$C_4$-alkenyloxycarbonyl, $C_2$-$C_4$-alkynyloxycarbonyl; wherein each of the foregoing substituents may be substituted by one or more halogen atoms, preferably fluorine atoms, where possible.

P may be optionally substituted phenyl, pyridyl, pyrrole, or pyrazole, e.g. optionally substituted with one to three substituents independently selected from $C_1$-$C_4$-alkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl, phenyl, phenyl-$C_1$-$C_4$-alkyl, $C_1$-$C_4$-alkoxy, $C_2$-$C_4$-alkenyloxy, $C_2$-$C_4$-alkynyloxy, $C_1$-$C_4$-alkoxy-$C_1$-$C_4$-alkyl, $C_1$-$C_4$-alkylthio, $C_1$-$C_4$-alkylsulfonyl, $C_1$-$C_4$-alkanoyl, hydroxyl, halogen (preferably fluorine), cyano, nitro, amino, $C_1$-$C_4$-alkylamino, $C_1$-$C_4$-dialkylamino, $C_1$-$C_4$-carbonyl, $C_1$-$C_4$-alkoxycarbonyl, $C_2$-$C_4$-alkenyloxycarbonyl, $C_2$-$C_4$-alkynyloxycarbonyl; wherein each of the foregoing substituents may be substituted by one or more halogen atoms, preferably fluorine atoms, where possible.

Preferably, P is phenyl, pyridyl, pyrrole, or pyrazole, each optionally substituted with one to three substituents independently selected from $C_1$-$C_4$-alkyl, $C_1$-$C_4$-haloalkyl (preferably $C_1$-$C_4$-fluoroalkyl) and halogen (preferably fluorine).

Preferably, P is pyrrole, or pyrazole, each optionally substituted with one to three substituents independently selected from $C_1$-$C_4$-alkyl, $C_1$-$C_4$-haloalkyl (preferably $C_1$-$C_4$-fluoroalkyl) and halogen (preferably fluorine).

Preferably, P is pyrazole optionally substituted with one to three substituents independently selected from $C_1$-$C_4$ alkyl, $C_1$-$C_4$ haloalkyl and halogen (preferably fluorine).

Preferably, P is group VIII or IX:

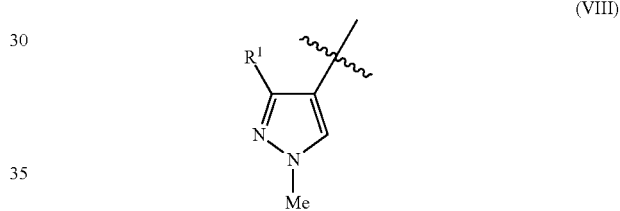

(VIII)

wherein $R^1$ is $CF_3$, $CHF_2$ or $CH_2F$;

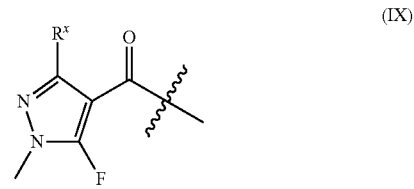

(IX)

wherein $R^x$ is selected from $CF_3$, $CHF_2$ and $CH_3$.

R may be hydrogen, alkyl, alkenyl, alkynyl, cycloalkyl, cycloalkyl-alkyl, aryl or heteroaryl; each of the foregoing may be optionally substituted.

R may be hydrogen, $C_1$-$C_4$-alkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl, phenyl, phenyl-$C_1$-$C_4$-alkyl or heteroaryl, e.g. as defined below; each of the foregoing may be optionally substituted with $C_1$-$C_4$-alkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl, phenyl, phenyl-$C_1$-$C_4$-alkyl, $C_1$-$C_4$— alkoxy, $C_2$-$C_4$-alkenyloxy, $C_2$-$C_4$-alkynyloxy, $C_1$-$C_4$-alkoxy-$C_1$-$C_4$-alkyl, $C_1$-$C_4$-alkylthio, $C_1$-$C_4$-alkylsulfonyl, $C_1$-$C_4$-alkanoyl, hydroxyl, halogen, cyano, nitro, amino, $C_1$-$C_4$-alkylamino, $C_1$-$C_4$-dialkylamino, $C_1$-$C_4$-carbonyl, $C_1$-$C_4$-alkoxycarbonyl, $C_2$-$C_4$-alkenyloxycarbonyl, $C_2$-$C_4$-alkynyloxycarbonyl; wherein each of the foregoing substituents may be substituted by one or more halogen atoms (preferably fluorine atoms) where possible.

Preferably, R is hydrogen or $C_1$-$C_4$ alkyl, preferably hydrogen or methyl, most preferably hydrogen.

Q may be optionally substituted aryl or optionally substituted heteroaryl, wherein aryl and heteroaryl are as defined below. In particular, Q may be optionally substituted phenyl or optionally substituted thienyl, e.g. optionally substituted as described below.

Preferably, Q is phenyl or 5-6 membered heteroaryl containing 1 or 2 heteroatoms independently selected from O, N and S, wherein the phenyl and heteroaryl are optionally substituted by one or more groups independently selected from halogen, $C_1$-$C_8$-alkyl, $C_1$-$C_8$-haloalkyl, $C_1$-$C_8$-alkoxy, cyano, hydroxyl, and amino; and wherein, in addition to the foregoing, the phenyl or heteroaryl is substituted at the ortho position with respect to X by a group selected from phenyl, $C_1$-$C_8$-alkyl, $C_1$-$C_8$-alkoxy, or $C_3$-$C_6$-cycloalkyl, and wherein each phenyl, $C_1$-$C_8$-alkyl, $C_1$-$C_8$-alkoxy, and $C_3$-$C_6$-cycloalkyl is optionally substituted by one or more, e.g. one to three, groups independently selected from halogen, $C_1$-$C_8$-alkyl, $C_1$-$C_8$-alkoxy, $C_3$-$C_6$-cycloalkyl, $C_1$-$C_8$-haloalkyl, $C_1$-$C_8$-haloalkoxy, and $C_3$-$C_6$-halocycloalkyl; or when Q is phenyl it is substituted at the ortho- and meta-position with respect to X by a fused bicyclo[2.2.1]heptane or bicyclo[2.2.1]heptene ring, each optionally substituted with one or more, e.g. one to three, groups independently selected from halogen, $C_1$-$C_8$-alkyl, $C_1$-$C_8$-haloalkyl, $C_1$-$C_8$-alkoxy, $C_1$-$C_8$-alkylthio, $C_1$-$C_8$-alkylamino, cyano, and hydroxyl, wherein any alkyl, haloalkyl, alkoxy, alkylthio, or alkylamino substituent may join with another alkyl, haloalkyl, alkoxy, alkylthio, or alkylamino substituent to form a ring, and/or the fused bicyclo[2.2.1]heptane or bicyclo[2.2.1]heptene ring is optionally substituted by $=N-N(R^{4b})R^{5b}$, wherein $R^{4b}$ and $R^{5b}$ are independently selected from $C_1$-$C_8$-alkyl, and/or the fused bicyclo[2.2.1]heptane or bicyclo[2.2.1]heptene ring is optionally substituted by $=C(R^{3a})R^{4a}$ wherein $R^{3a}$ and $R^{4a}$ are independently selected from $C_1$-$C_8$ alkyl and $C_1$-$C_8$ haloalkyl.

Preferably, Q is phenyl or a 5-6 membered heteroaryl containing 1 or 2 heteroatoms independently selected from O, N and S, wherein the phenyl and heteroaryl are optionally substituted by one or more groups independently selected from fluorine, $C_1$-$C_8$-alkyl, $C_1$-$C_8$-fluoroalkyl, $C_1$-$C_8$-alkoxy, cyano, hydroxyl, and amino; and wherein, in addition to the foregoing, the phenyl or heteroaryl is substituted at the ortho position with respect to X by phenyl, $C_1$-$C_8$-alkyl, $C_1$-$C_8$-alkoxy, or $C_3$-$C_6$-cycloalkyl, and wherein each phenyl, $C_1$-$C_8$-alkyl, $C_1$-$C_8$-alkoxy, and $C_3$-$C_6$-cycloalkyl is optionally substituted by one or more groups independently selected from fluorine, $C_1$-$C_8$-alkyl, $C_1$-$C_8$-alkoxy, $C_3$-$C_6$-cycloalkyl, $C_1$-$C_8$-fluoroalkyl, $C_1$-$C_8$-fluoroalkoxy, and $C_3$-$C_6$ fluorocycloalkyl; or when Q is a phenyl it is substituted at the ortho- and meta-position with respect to X by a fused bicyclo[2.2.1]heptane or bicyclo[2.2.1]heptene ring, each optionally substituted with one or more, e.g. one to three, groups independently selected from fluorine, $C_1$-$C_8$-alkyl, $C_1$-$C_8$-fluoroalkyl, $C_1$-$C_8$-alkoxy, $C_1$-$C_8$-alkylthio, $C_1$-$C_8$-alkylamino, cyano, hydroxyl, and amino-$C_1$-$C_4$ alkyl, wherein any alkyl, fluoroalkyl, alkoxy, alkylthio, or alkylamino substituent may join with another alkyl, alkoxy, alkylthio, or alkylamino substituent to form a ring, and/or the fused bicyclo[2.2.1]heptane or bicyclo[2.2.1]heptene ring is optionally substituted by $=N-N(R^{4b})R^{5b}$, wherein $R^{4b}$ and $R^{5b}$ are independently selected from $C_1$-$C_8$-alkyl, and/or the fused bicyclo[2.2.1]heptane or bicyclo[2.2.1]heptene ring is optionally substituted by $=C(R^{3a})R^{4a}$ wherein $R^{3a}$ and $R^{4a}$ are independently selected from $C_1$-$C_8$ alkyl and $C_1$-$C_8$ fluoroalkyl.

Preferably Q is phenyl or thienyl, each optionally substituted by one to three halogen atoms, preferably one to three fluorine atoms, wherein in addition to the foregoing, the phenyl or thienyl group is substituted at the ortho position with respect to X by $C_1$-$C_8$-alkyl, $C_1$-$C_8$ fluoroalkyl, $C_3$-$C_6$-cycloalkyl, $C_3$-$C_6$-cycloalkyl optionally substituted by $C_3$-$C_6$ cycloalkyl, phenyl, phenyl optionally substituted by one to three halogen atoms, preferably one to three fluorine atoms, or phenyl substituted at the ortho- and meta-position with respect to X by a fused bicyclo[2.2.1]heptane or bicyclo[2.2.1]heptene ring, each optionally substituted by $C_1$-$C_8$-alkyl, $C_1$-$C_8$-fluoro alkyl, $C_1$-$C_8$-alkoxy, $C_1$-$C_8$-alkylthio, $C_1$-$C_8$-alkylamino, wherein any alkyl, fluoroalkyl, alkoxy, alkylthio, or alkylamino substituent may join with another alkyl, alkoxy, alkylthio, or alkylamino substituent to form a ring, and/or the fused bicyclo[2.2.1]heptane or bicyclo[2.2.1]heptene ring is optionally substituted by $=N-N(R^{4b})R^{5b}$, wherein $R^{4b}$ and $R^{5b}$ are independently selected from $C_1$-$C_8$-alkyl, and/or the fused bicyclo[2.2.1]heptane or bicyclo[2.2.1]heptene ring is optionally substituted by $=C(R^{3a})R^{4a}$ wherein $R^{3a}$ and $R^{4a}$ are independently selected from $C_1$-$C_8$ alkyl and $C_1$-$C_8$ fluoroalkyl.

Preferably Q is group V, group VI or group VIIa, group VIIb or group VIIc:

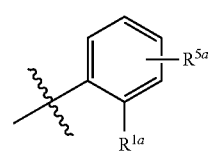

(V)

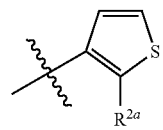

(VI)

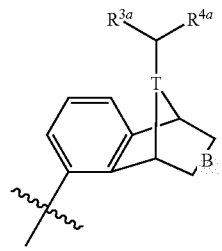

(VIIa)

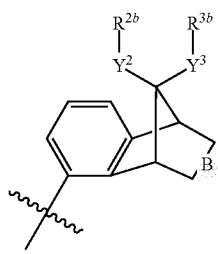

(VIIb)

-continued

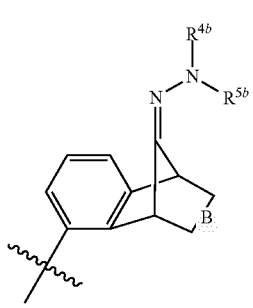
(VIIc)

B is a single or double bond;
T is a single or double bond;
$R^{1a}$ is phenyl optionally substituted with one to three halogen atoms (preferably fluorine atoms), or $R^{1a}$ is $C_1$-$C_8$-alkyl, $C_1$-$C_8$-haloalkyl (preferably $C_1$-$C_8$-fluoroalkyl) or

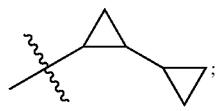 [SMILES: *C1CC1C1CC1]

$R^{2a}$, $R^{3a}$ and $R^{4a}$ are each independently $C_1$-$C_8$-alkyl or $C_1$-$C_8$-haloalkyl (preferably $C_1$-$C_8$-fluoroalkyl);
$Y^2$ and $Y^3$ are independently O, S, N;
$R^{2b}$ and $R^{3b}$ are independently $C_1$-$C_8$-alkyl, wherein $R^{2b}$ and $R^{3b}$ are optionally joined to form a 5-8 membered ring;
$R^{4b}$ and $R^{5b}$ are independently $C_1$-$C_8$-alkyl;
$R^{5a}$ is hydrogen or halogen, preferably hydrogen or fluorine.

Preferably, Q is a group VIIa, group VIIb or group VIIc, more preferably group VIIa.

In general, it is preferred that P, Q and R do not have any Cl, Br or I substituent other than e.g. substituent X on Q.

Generally, the term aryl includes aromatic hydrocarbon rings such as phenyl, naphthyl, anthracenyl, phenanthrenyl. The term heteroaryl includes aromatic ring systems comprising mono-, bi- or tricyclic systems wherein at least one oxygen, nitrogen or sulfur atom is present as a ring member. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

The above aryl, heteroaryl groups may carry one or more non-aromatic fused ring systems, e.g. 1,2-fused ring systems. The aryl, heteroaryl and fused ring systems may carry one or more, e.g. 3, identical or different substituents.

Examples of optional substituents of aryl, heteroaryl and fused ring groups are: alkyl, alkenyl, alkynyl, cycloalkyl, cycloalkyl-alkyl, phenyl and phenyl-alkyl, alkoxy, alkenyloxy, alkynyloxy, alkoxyalkyl, alkylthio, alkylsulfonyl, formyl, alkanoyl, hydroxyl, halogen, cyano, nitro, amino, alkylamino, dialkylamino, carbonyl, alkoxycarbonyl, alkenyloxycarbonyl, alkynyloxycarbonyl; each of the preceding substituents may be substituted by one or more halogen atoms where possible.

For example, the optional substituents of aryl, heteroaryl and fused ring groups may be $C_1$-$C_4$-alkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl, phenyl, phenyl-$C_1$-$C_4$-alkyl, $C_1$-$C_4$-alkoxy, $C_2$-$C_4$-alkenyloxy, $C_2$-$C_4$-alkynyloxy, $C_1$-$C_4$-alkoxy-$C_1$-$C_4$-alkyl, $C_1$-$C_4$-alkylthio, $C_1$-$C_4$-alkylsulfonyl, $C_1$-$C_4$-alkanoyl, hydroxyl, halogen, cyano, nitro, amino, $C_1$-$C_4$-alkylamino, $C_1$-$C_4$-dialkylamino, $C_1$-$C_4$-carbonyl, $C_1$-$C_4$-alkoxycarbonyl, $C_2$-$C_4$-alkenyloxycarbonyl, $C_2$-$C_4$-alkynyloxycarbonyl; wherein each of the preceding substituents may be substituted by one or more halogen atoms where possible.

The term "sulphonate" is art recognized and includes a moiety that can be represented by the general formula:

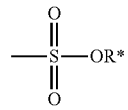

in which R* is an electron pair, hydrogen, alkyl, cycloalkyl, or aryl. For example, X may be triflate, tosylate, mesylate, or nonaflate, e.g. it may be trifluoromethanesulfonate ester, p-toluenesulfonate ester, methanesulfonate, or nonafluorobutanesulfonate ester. In particular, X may be tosylate or mesylate.

Carbon chains, e.g. alkyl and/or alkoxy, may be branched or unbranched.

The term halogen refers to F, Cl, Br, or I. Preferably any halogen substituent, other than e.g. X, is a fluorine substituent.

In a further aspect of the invention, there is provided a method of preparing a compound of formula IC comprising performing the reaction represented by scheme 1C:

Scheme 1C

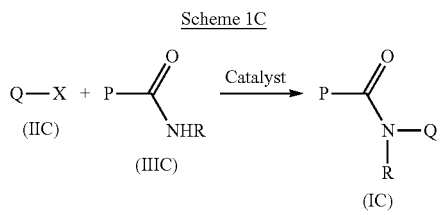

wherein

Q is optionally substituted aryl or optionally substituted heteroaryl;

X is chlorine;

R is hydrogen;

P is group VIII or IX:

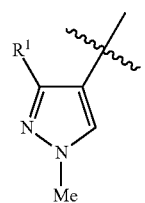
(VIII)

wherein $R^1$ is $CF_3$, $CHF_2$ or $CH_2F$;

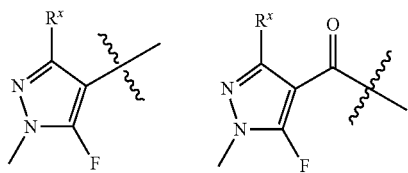

wherein $R^x$ is selected from $CF_3$, $CHF_2$ and $CH_3$;
wherein the catalyst comprises copper and a ligand.

Preferably the reaction is performed in an organic polar solvent.

In a further aspect of the invention, there is provided a method of preparing a compound of formula ID comprising performing the reaction represented by scheme 1D:

Scheme 1D

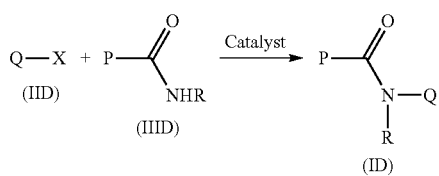

wherein Q is group V, group VI or group VIIa, group VIIb or group VIIc:

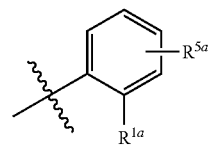
(V)

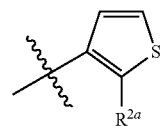
(VI)

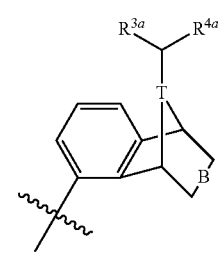
(VIIa)

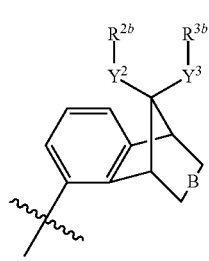
(VIIb)

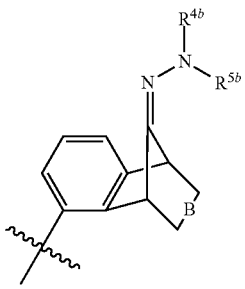
(VIIc)

B is a single or double bond;
T is a single or double bond;
$R^{1a}$ is phenyl optionally substituted with one to three halogen atoms (preferably fluorine atoms), or $R^{1a}$ is $C_1$-$C_8$-alkyl, $C_1$-$C_8$-haloalkyl (preferably $C_1$-$C_8$-fluoroalkyl) or

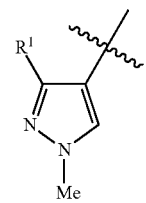;

$R^{2a}$, $R^{3a}$ and $R^{4a}$ are each independently $C_1$-$C_8$-alkyl or $C_1$-$C_8$-haloalkyl (preferably $C_1$-$C_8$-fluoroalkyl);
$Y^2$ and $Y^3$ are independently O, S, N;
$R^{2b}$ and $R^{3b}$ are independently $C_1$-$C_8$-alkyl, wherein $R^{2b}$ and $R^{3b}$ are optionally joined to form a 5-8 membered ring;
$R^{4b}$ and $R^{5b}$ are independently $C_1$-$C_8$-alkyl;
$R^{5a}$ is hydrogen or halogen, preferably hydrogen or fluorine;
X is chlorine;
R is hydrogen;
P is group VIII or IX:

(VIII)

(IX)

wherein $R^1$ is $CF_3$, $CHF_2$ or $CH_2F$;

wherein $R^x$ is selected from $CF_3$, $CHF_2$ and $CH_3$;
wherein the catalyst comprises copper and a ligand.

Preferably the reaction is performed in an organic polar solvent.

In a further aspect of the invention, there is provided a method of initiating a reaction represented by scheme 1E:

Scheme 1E

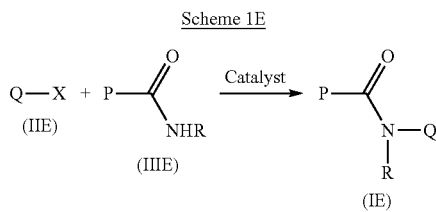

wherein

Q is optionally substituted aryl or optionally substituted heteroaryl;

X is chlorine;

R is hydrogen;

P is group VIII or IX:

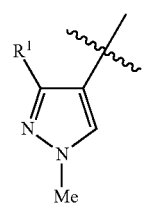
(VIII)

wherein $R^1$ is $CF_3$, $CHF_2$ or $CH_2F$;

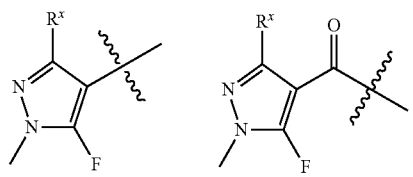
(IX)

wherein $R^x$ is selected from $CF_3$, $CHF_2$ and $CH_3$;

wherein the catalyst comprises copper and a ligand; and wherein the method comprises providing the compound of formula III in liquid form prior to contacting the compound of formula IIIE with the catalyst.

In a further aspect of the invention, there is provided a method of initiating a reaction represented by scheme 1F:

Scheme 1F

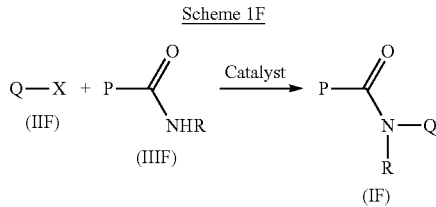

wherein

Q is group V, group VI or group VIIa, group VIIb or group VIII:

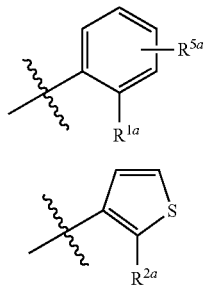
(V)

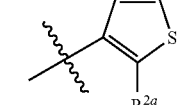
(VI)

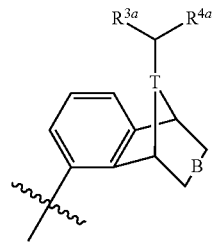
(VIIa)

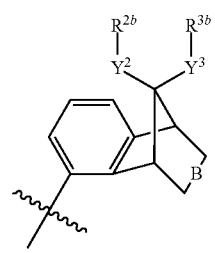
(VIIb)

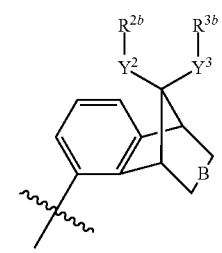
(VIIc)

B is a single or double bond;
T is a single or double bond;
$R^{1a}$ is phenyl optionally substituted with one to three halogen atoms (preferably fluorine atoms), or $R^{1a}$ is $C_1$-$C_8$-alkyl, $C_1$-$C_8$-haloalkyl (preferably $C_1$-$C_8$-fluoroalkyl) or

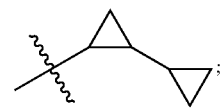 [SMILES: *C1CC1C1CC1];

$R^{2a}$, $R^{3a}$ and $R^{4a}$ are each independently $C_1$-$C_8$-alkyl or $C_1$-$C_8$-haloalkyl (preferably $C_1$-$C_8$-fluoroalkyl);
$Y^2$ and $Y^3$ are independently O, S, N;
$R^{2b}$ and $R^{3b}$ are independently $C_1$-$C_8$-alkyl, wherein $R^{2b}$ and $R^{3b}$ are optionally joined to form a 5-8 membered ring;
$R^{4b}$ and $R^{5b}$ are independently $C_1$-$C_8$-alkyl;
$R^{5a}$ is hydrogen or halogen, preferably hydrogen or fluorine;
X is chlorine;
R is hydrogen;

P is group VIII or IX:

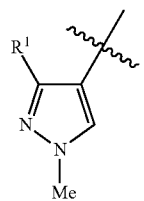

(VIII)

wherein R¹ is $CF_3$, $CHF_2$ or $CH_2F$;

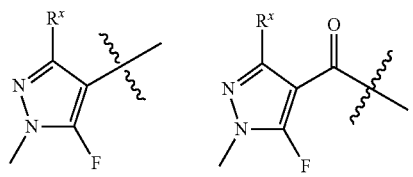

(IX)

wherein $R^x$ is selected from $CF_3$, $CHF_2$ and $CH_3$;
wherein the catalyst comprises copper and a ligand; and
wherein the method comprises providing the compound of formula III in liquid form prior to contacting the compound of formula IIIF with the catalyst.

Preferably the copper is provided in a soluble form. The copper may be a copper atom or ion, e.g. it may be in a (0), (I) or (II) oxidation state. Preferably the copper is provided in a (I) oxidation state.

The copper may derived from a copper salt. For example, the copper may be provided as CuCl, CuBr, CuI, $Cu_2O$, CuSCN, $CuCl_2$, $CuBr_2$, $CuI_2$, CuO, $CuSCN_2$ or a mixture thereof. Preferably, the copper is provided as CuCl, CuBr, CuI or a mixture thereof. The term "copper" refers to any form of copper (0), (I), (II) (III) e.g. a copper salt, copper solvated ion or atom and/or copper complex.

The ligand may be alkyl alcohol, aryl alcohol e.g. phenol, alkyl amine, diamine e.g. 1,2-diamine, or 1,3 diamine, 1,2-aminoalcohol, 1,2-aminoether e.g. tris(3,6,-dioxaheptyl) amine, 1,2-aminoacid e.g. pipecolinic acid, 1,2-diol, imidazolium carbene, pyridine, 1,10-phenanthroline, 1,3-diketone e.g. 2,4-pentadione; each optionally substituted. Preferably the ligand is a diamine, e.g. an optionally substituted 1,2- or 1,3-diamine and/or an optionally substituted 1,10-phenanthroline. Each of the foregoing may be optionally substituted.

For example, the ligand may be 1,2-diaminoalkane, 1,3-diaminoalkane, 1,2-diaminocyclohexane, 1,10-phenanthroline, 2-hydroxyethyl amine, or 1,2-diaminoethane, each optionally substituted. Preferably the ligand is optionally substituted 1,2-diaminocyclohexane such as 1,2-diaminocyclohexane, N,N-dimethyl-1,2-diaminocyclohexane, and/or N-tolyl-1,2-diaminocyclohexane.

For example, the ligand may be N,N,N',N'-tetramethyl-1,2-diaminoethane, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, (methylimino)diacetic acid, ethanolamine, 1,2-diaminoethane, N,N'-dimethyl-1,2-diaminoethane, N,N'-dimethylethylenediamine, ethylenediamine, N-methylethylenediamine, N-butylethylenediamine, N,N,N'-trimethylethylenediamine, tetra-n-butylammoniumfluoride, and/or tris(3,6-trioxaheptyl)amine. Preferably the ligand is N,N' dimethyl 1,2 diamine cyclohexane, N,N' dimethyl 1,2 diethylamine, or N1-methyl-propane-1,3-diamine.

Where isomers of a particular ligand are possible, e.g. cis-trans isomers and/or stereoisomers, the ligand may be one particular isomer, e.g. a cis or trans isomer, or a mixture of isomers may be employed. For example, where the ligand comprised by the catalyst is 1,2-diaminocyclohexane, the ligand may be cis-1,2-diaminocyclohexane, trans-1,2-diaminocyclohexane, or a mixture of cis- and trans-1,2 diaminocyclohexane.

The ligand may be trans-N,N'-dimethyl-1,2-diaminocyclohexane. Preferably the molar ratio of trans-N,N'-dimethyl-1,2-diaminocyclohexane to cis-N,N'-dimethyl-1,2-diaminocyclohexane in the reaction mixture is at least 55% to 45%, at least 60% to 40%, at least 70% to 30%, at least 80% to 20%, at least 90% to 10%, at least 95% to 5%, at least 99% to 1%. In some cases the ligand may be substantially all trans-N,N'-dimethyl-1,2-diaminocyclohexane, e.g. 100% trans-N,N'-dimethyl-1,2-diaminocyclohexane.

For the avoidance of doubt, the general term "optionally substituted" means substituted or not substituted with one or more groups. For example "optionally substituted 1,2-diamine" means 1,2-diamine or substituted 1,2-diamine. "Substituted 1,2-diamine" includes 1,2-diamines substituted with one or more (functional) groups.

Generally, the molar ratio of ligand to copper may be at least 10 to 1, at least 5 to 1, at least 3 to 1, at least 2.5 to 1, at least 2 to 1, at least 1.5 to 1, at least 1 to 1, at least 0.5 to 1, at least 0.1 to 1. For example, the molar ratio of ligand to copper may be less than 10 to 1, less than 5 to 1, less than 3 to 1, less than 2.5 to 1, less than 2 to 1, less than 1.5 to 1, or less than 1 to 1. For example, the molar ratio of ligand to copper may be in the range from 10:0.1 to 0.1:10, 5:1 to 1:5, 3:1 to 1:3, 2.5:1 to 1:2.5, 2:1 to 1:2, or 1.5:1 to 1:1.5. Preferably the molar ratio of ligand to copper is at least 1 to 1, e.g. at least 2 to 1, e.g. about 2.2 to 1.

Additional ligand may be added to the reaction mixture after the reaction has commenced, e.g. at one or more time points after commencement. Additional ligand may be added batch-wise, continuously or by a combination of both methods. Additional ligand may be added, for example, after at least 10, at least 20, at least 30, at least 40, at least 50, or at least 60 minutes, e.g. after at least 1, at least 2, at least 3, at least 4, or at least 5, hours after commencement. The molar amount of additional ligand added during the course of the reaction may be at least 0.1, at least 0.5, at least 1, at least 2, at least 3, at least 4, at least 5, at least 8, or even at least 10 times the molar amount of copper present at reaction commencement. For example, at commencement of the reaction the ligand may be present at about the same molar concentration as the copper, with additional ligand added during the reaction so that the final molar concentration of the ligand is at least 2, at least 2.5, at least 3, at least 3.5, at least 4, at least 4.5, at least 5, at least 8, or even at least 10 times the molar concentration of the copper.

Likewise, additional copper may be added to the reaction mixture after the reaction has commenced, e.g. at one or more time points after commencement. Additional copper may be added batch-wise, continuously or by a combination of both methods. Additional copper may be added, for example, after at least 10, at least 20, at least 30, at least 40, at least 50, or at least 60 minutes, e.g. after at least 1, at least 2, at least 3, at least 4, or at least 5, hours after commencement. The molar amount of additional copper added during the course of the reaction may be at least 0.1, at least 0.5, at least 1, at least 2, at least 3, at least 4, at least 5, at least 8, or even at least 10 times the amount of copper present at commencement of the reaction. The final molar concentration of the copper may be at least 2, at least 2.5, at least 3, at least 3.5, at least 4, at least 4.5, at least 5, at least 8, or even at least 10 times the molar concentration of the copper at reaction commencement.

In the same way, additional copper and ligand may be added to the reaction mixture after the reaction has commenced, e.g. simultaneously, sequentially or separately. For additional reaction safety the compound of formula (II) may be slowly added to the reaction. The solvent and/or water may be distilled off during the reaction. The solvent may then be recharged, e.g. to maintain reaction mobility.

The reaction may be performed using a solvent that has a boiling point (as determined under standard conditions) above 100° C., above 110° C., above 120° C., above 130° C., above 140° C., above 150° C., above 160°, or even above 170° C. Preferably, the reaction of the invention is performed using a solvent that has a boiling point above 150° C.

The solvent is preferably an organic polar solvent, i.e. the solvent contains at least one carbon atom. The solvent may be protic or aprotic. Examples of solvents include ethers, such as diethylether, 1,2-dimethoxyethane, diethoxymethane, diglyme, t-butyl methyl ether, THF, 2-methyl-THF, dioxane; halogenated solvents such as chloroform, dichloromethane, dichloroethane, monochlorobenzene, dichlorobenzene, trichlorobenzene, 4-fluorotoluene; esters and ketones such as ethyl acetate, acetone 2-butanone, methylisobutylketone; amines such as anisole, polar aprotic solvents such as acetonitrile, dimethylsulfoxide, dimethylformamide, N-methylpyrrolidone, dimethylacetamide; and alcohols, such as methanol, ethanol, isopropanol, t-BuOH, cyclohenxanol, heptanol, octanol, or longer chain alcohols, and diethyleneglycol. A combination of more than one solvent may be employed, which may include one or more non-polar solvents.

Preferably the solvent is selected from the group consisting of alcohols, ethers, esters, ketones, halogenated solvents, amines, amides, nitriles, and sulfoxides, e.g. alcohols, ethers, ketones, amines, amides, nitriles, and sulfoxides. More preferably the solvent is selected from alcohols, straight and branched chain ethers, amines and ketones, e.g. alcohols, straight and branched chain ethers, and ketones. Preferably the solvent is diglyme, ethyl diglyme, DMF, NMP, cyclohexanol, cyclohenanone, or tBuOH. In some embodiments the solvent is the compound of formula II.

When X is halide the solvent may be one in which halide salts have low solubility in which salts are substantially insoluble so that the halide ions released during the reaction are substantially removed from the reaction solution. Alternatively a combination of solvents may be used to tune the bulk solvent polarity verses halide salt solvation whereby one or more polar solvents, particularly polar aprotic solvents, and/or one or more non-polar solvents are combined. An example is a mixture of DMF with xylene, which may in some cases contain about 50% v/v of each solvent.

Preferably, the reaction is performed in the presence of a base. The base may be any Bronsted base, e.g. a carbonate, carboxylate, phosphate, oxide, hydroxide, alkoxide, aryloxide, amine, metal amide, fluoride, or guanidine, or a mixture of one or more thereof. The base may be a metal salt of a carboxylic acid, e.g. sodium acetate. Examples of suitable bases include $K_3PO_4$, $K_2CO_3$, $Na_2CO_3$, $Ti_2CO_3$, $Cs_2CO_3$, K(OtBu), Li(OtBu), Na(OtBu), K(OPh), Na(OPh), or mixtures thereof. Preferably the base is a carbonate, e.g. potassium carbonate. The skilled person will readily be able to determine the amount of base needed.

The reaction may be carried out at a temperature of 0 to 200° C., in particular at least 100° C., at least 110° C., at least 120° C., at least 130° C., at least 140° C., at least 150° C., at least 160° C., at least 170° C., at least 180° C., or even at least 190° C. The reaction may be performed in the range of from 0° C.-200° C., 100° C.-200° C., 110-200° C., 120° C.-200° C., 130° C.-200° C., 140° C.-200° C., 150° C.-200° C., 160° C.-200° C., 170° C.-200° C., 180° C.-200° C., 190° C.-200° C., 100° C.-190° C., 100° C.-180° C., 100° C.-170° C., 120° C.-160° C., 130° C.-190° C., 140° C.-180° C., 140° C.-170° C., 140° C.-160° C., or in the range from 145° C.-155° C.

The reaction may be performed at a higher pressure than atmospheric pressure. For example, the reaction may be performed at a pressure of about 1 bar or at least 1.1 bar, at least 1.2 bar, at least 1.3 bar, at least 1.4 bar, at least 1.5 bar, at least 1.6 bar, at least 1.7 bar, at least 1.8 bar, at least 1.9 bar, at least 2 bar, at least 3 bar, at least 4 bar, or even at least 5 bar, e.g. less than 10 bar, less than 5 bar, less than 2 bar, e.g. in the range of from 1 bar to 10 bar, 1 bar to 5 bar, 1 bar to 4 bar, 1 bar to 3 bar, 1 bar to 2 bar, 1 bar 1.9 bar, 1 bar to 1.8 bar, 1 bar to 1.7 bar, 1 bar to 1.6 bar, 1 bar to 1.5 bar, 1 bar to 1.4 bar, 1 bar to 1.3 bar, 1 bar to 1.2 bar, or even from 1 bar to 1.1 bar. A higher pressure than 1 bar may be used when the solvent chosen has a boiling point less than the desired reaction temperature. For the present purposes 1 bar may be generally considered to represent atmospheric pressure.

Provision may be made for removal, e.g. continuous removal, of water from the reaction mixture. A suitable method is azeotropic removal of water. Suitable apparatus for conducting azeotropic removal of water will be known to those skilled in the art.

The amount of copper employed may be less than 50 mol % based on the amount of compound (II), e.g. less than 25 mol %, less than 20 mol %, less than 10 mol %, less than 5 mol %, less than 2 mol %, less than 1 mol %, less than 0.5 mol %, or less than 0.1 mol % based on the amount of compound (II). The amount of copper employed may be at least 0.01 mol % based on the amount of compound (II), e.g. at least 0.1 mol %, at least 1, at least 2, at least 5, or at least 10 mol % based on the amount of compound (II). The amount of copper employed may be in the range from 0.01 to 50 mol % based on the amount of compound (II), in the range from 0.1 to 25 mol %, 1 to 20 mol %, or in the range from 5 to 15 mol % based on the amount of compound (II). Preferably, the amount of copper is about 1 mol % based on the amount of compound (II), but may be up to 20 mol %.

The amount of copper employed may be less than 50 mol % based on the amount of compound (III), e.g. less than 25 mol %, less than 20 mol %, less than 10 mol %, less than 5 mol %, less than 2 mol %, less than 1 mol %, less than 0.5 mol %, or less than 0.1 mol % based on the amount of compound (III). The amount of copper employed may be at least 0.01 mol % based on the amount of compound (III), e.g. at least 0.1 mol %, at least 1, at least 2, at least 5, or at least 10 mol % based on the amount of compound (III). The amount of copper employed may be in the range from 0.01 to 50 mol % based on the amount of compound (III), in the range from 0.1 to 25 mol %, 1 to 20 mol %, or in the range from 5 to 15 mol % based on the amount of compound (III). Preferably the amount of copper is about 1 mol % based on the amount of compound (III), but may be up to 20 mol %.

The amount of ligand employed may be less than 100 mol %, based on the amount of compound (II), e.g. less than 50 mol %, less than 25 mol %, less than 20 mol %, less than 10 mol %, less than 5 mol %, less than 2 mol %, less than 1 mol %, less than 0.5 mol %, or even less than 0.1 mol % based on the amount of compound (II). The amount of ligand employed may be at least 0.01 mol % based on the amount of compound (II), e.g. at least 0.1 mol %, at least 1 mol %, at least 2 mol %, at least 5 mol %, at least 10 mol %, at least 20 mol %, or at least 50 mol % based on the amount of compound (II). The amount of ligand employed may be in the range from 0.01 to 100 mol % based on the amount of compound (II), in the range from 1 to 50 mol %, 5 to 40 mol %, 10 to 30 mol %, or in the range from 15 to 25 mol % based on the amount of compound (II).

The amount of ligand employed may be less than 100 mol %, based on the amount of compound (III), e.g. less than 50 mol %, less than 25 mol %, less than 20 mol %, less than 10 mol %, less than 5 mol %, less than 2 mol %, less than 1 mol %, less than 0.5 mol %, or even less than 0.1 mol % based on the amount of compound (III). The amount of ligand employed may be at least 0.01 mol % based on the amount of compound (III), e.g. at least 0.1 mol %, at least 1 mol %, at least 2 mol %, at least 5 mol %, at least 10 mol %, at least 20 mol %, or at least 50 mol % based on the amount of compound (III). The amount of ligand employed may be in the range from 0.01 to 100 mol % based on the amount of compound (III), in the range from 1 to 50 mol %, 5 to 40 mol %, 10 to 30 mol %, or in the range from 15 to 25 mol % based on the amount of compound (III).

In the reaction of the invention, the molar ratio of compound (II) to (III) may be in the range of from 10:1 to 1:10, 5:1 to 1:5, 2:1 to 1:2 or 1.2:1 to 1:1.2. Preferably compound (II) is in molar excess compared to compound (III). Preferably the molar ratio of (II) to (III) is at least 1.1:1, 1.5:1, 2:1, 3:1, or even at least 4:1.

However, the reactants may be fed one to the other over the course of the reaction in which case the ratio of reactants may vary considerably during the course of the reaction.

Workup of the reaction mixture is achieved according to well known procedures of synthetic organic chemistry. For example, an aqueous workup may be achieved by the addition of water (or other aqueous solution), and filtering the product as a precipitate or extraction of the desired product with a suitable organic solvent. Alternatively, the product may be isolated by removing any solvent present by distillation, e.g. under reduced pressure. Purification of the product may be achieved by any one of a number of methods, e.g. distillation, recrystallization and chromatography.

In one embodiment the invention relates to a method of preparing the compounds described in WO 04/035589, e.g. compounds of formula (X):

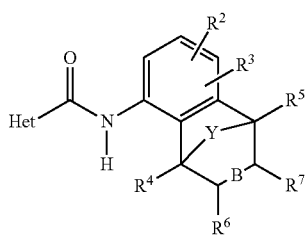

(X)

where Het is pyrrolyl or pyrazolyl being substituted by groups $R^8$, $R^9$ and $R^{10}$;
Y is $CR^{12}R^{13}(CHR^{14}R^{15})_m(CHR^{16}R^{17})_n$, $CY^2(R^{2b})Y_3(R^{3b})$ or $C=N-NR^{4b}(R^{5b})$;
$Y^2$ and $Y^3$ are, independently, O, S, N;
$R^{2b}$ and $R^{3b}$ are, independently, $C_1$-$C_8$-alkyl, wherein $R^{2b}$ and $R^{3b}$ are optionally joined to form a 5-8 membered ring;
$R^{4b}$ and $R^{5b}$ are, independently, $C_1$-$C_8$-alkyl;
B is a single bond or a double bond;
m is 0 or 1;
n is 0 or 1;
$R^2$ and $R^3$ are each, independently, hydrogen, halogen, $C_1$-$C_4$-alkyl, $C_1$-$C_4$-alkoxy or $C_1$-$C_4$-haloalkoxy;
$R^4$, $R^5$, $R^6$ and $R^7$ are each, independently, hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, hydroxymethyl, $C_1$-$C_4$-alkoxymethyl, $C(O)CH_3$ or $C(O)OCH_3$;

$R^8$, $R^9$ and $R^{10}$ are each, independently, hydrogen, halogen, cyano, nitro, $C_1$-$C_4$-alkyl, $C_1$-$C_4$-haloalkyl, $C_1$-$C_4$-alkoxy ($C_1$-$C_4$)alkylene or $C_1$-$C_4$-haloalkoxy($C_1$-$C_4$)alkylene, provided that at least one of $R^8$, $R^9$ and $R^{10}$ is not hydrogen;
$R^{12}$ and $R^{13}$ are each, independently, hydrogen, halogen, $C_1$-$C_6$-alkyl, $C_1$-$C_6$-alkoxy, $CH_2OH$, $CH(O)$, $C_3$-$C_6$-cycloalkyl, $CH_2O-C(=O)CH_3$, $CH_2-C_3$-$C_6$-cycloalkyl or benzyl;
or $R^{12}$ and $R^{13}$ together with the carbon atom to which they are attached form the group $C=O$ or a 3-5 membered carbocyclic ring;
or $R^{12}$ and $R^{13}$ together form $C_1$-$C_6$-alkylidene or $C_3$-$C_6$-cycloalkylidene; and
$R^{14}$, $R^{15}$, $R^{16}$ and $R^{17}$ are each, independently, H or $C_1$-$C_6$-alkyl;
comprising the step of reacting a compound of formula (XI):

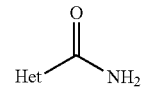

(XI)

wherein Het is as defined for the compound of formula (X); with a compound of formula (XII):

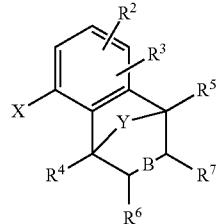

(XII)

wherein Y, B, $R^2$, $R^3$, $R^4$, $R^5$, $R^6$, $R^7$ are as defined for the compound of formula (X), X is F, Cl, Br, I, or a sulphonate;
$R^8$, $R^9$ and $R^{10}$ may be each, independently, hydrogen, chloro, fluoro, methyl, $CF_3$, $CHF_2$ or $CH_2F$, provided that at least one of $R^8$, $R^9$ and $R^{10}$ is not hydrogen m and n may both be 0.
$R^{12}$ and $R^{13}$ may be each, independently, hydrogen, $C_1$-$C_4$-alkyl or $C_1$-$C_4$-alkoxy.
$R^{14}$ and $R^{15}$ may both be $CH_3$.
$R^2$ may be hydrogen, halogen or $C_1$-$C_4$-alkyl.
$R^3$ may be hydrogen or methyl.
$R^4$, $R^5$, $R^6$ and $R^7$ may be hydrogen.
Het may be pyrazolyl or pyrrolyl, preferably pyrazolyl.

The invention includes methods of preparing isomers of compounds of formula (X), including stereoisomers, geometric isomers and any tautomers. In particular, the invention includes methods of preparing the stereoisomers of compounds of the formula (X), e.g. compounds in which the Y moiety is above or below the plane of the aromatic ring. The invention also includes methods of preparing salts of the compound of formula (X). Generally, any reference to a particular compound includes references to any stereoisomers, geometric isomers, tautomers, and salts of the compound unless otherwise stated.

It will be clear to the skilled person that when m is 1 and n is 1, $R^{12}$ and $R^{13}$ are absent. When m is 1 and n is 0, or m is 0 and n is 1, $R^{12}$ is absent and $R^{13}$ is present or vice versa. When m is 0 and n is 0, $R^{12}$ and $R^{13}$ are both present.

It will be clear that the compound of formula (X) corresponds to the compound of formula (I) in scheme 1, the compound of formula (XI) corresponds to the compound of formula (III) in scheme I and the compound of formula (XII) corresponds to the compounds of formula (II) in scheme 1.

In a further embodiment the invention relates to a reaction comprising preparing a compound of formula XX:

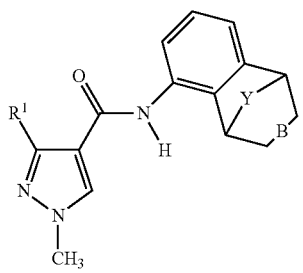

(XX)

wherein:
Y is $CR^{12}R^{13}(CHR^{14}R^{15})_m(CHR^{16}R^{17})_n$, $CY^2(R^{2b})Y^3(R^{3b})$, or $C=N-NR^{4b}(R^{5b})$;
B is a single bond or a double bond;
$Y^2$ and $Y^3$ are, independently, O, S, N;
$R^{2b}$ and $R^{3b}$ are, independently, $C_1$-$C_8$ alkyl, wherein $R^{2b}$ and $R^{3b}$ are optionally joined to form a 5-8 membered ring;
$R^{4b}$ and $R^{5b}$ are, independently, $C_1$-$C_8$ alkyl;
m is 0 or 1;
n is 0 or 1;
$R^{12}$ and $R^{13}$ are each, independently, hydrogen, halogen, $C_1$-$C_6$ alkyl, $C_1$-$C_6$ alkoxy, CH(O), $C_3$-$C_6$ cycloalkyl, $CH_2O-C(=O)CH_3$, $CH_2-C_3$-$C_6$ cycloalkyl or benzyl;
or $R^{12}$ and $R^{13}$ together with the carbon atom to which they are attached form the group C=O or a 3-5 membered carbocyclic ring;
or $R^{12}$ and $R^{13}$ together form $C_{3-6}$ cycloalkylidene;
$R^{14}$, $R^{15}$, $R^{16}$ and $R^{17}$ are each, independently, hydrogen or $C_1$-$C_6$ alkyl;
$R^1$ is $C_1$-$C_4$ haloalkyl;
comprising the step of reacting a compound of formula XXI:

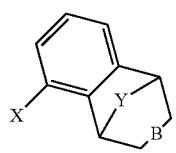

(XXI)

wherein:
X is a leaving group, such as F, Cl, Br, I, or a sulphonate;
Y and B are as defined for the compound of formula XX;
with a compound of formula XXII:

(XXII)

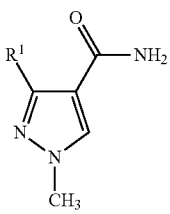

wherein $R^1$ is $C_1$-$C_4$ haloalkyl;

In a further embodiment the invention relates to a reaction comprising preparing a compound of formula XXA:

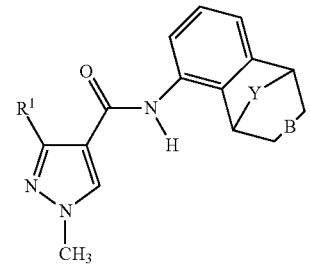

(XXA)

which are compounds of formula XX wherein
Y is $CHCHR^{18}(R^{19})$ or $C=C(A)Z$, $CY^2(R^{2b})Y^3(R^{3b})$, $C=N-NR^{4b}(R^{5b})$;
$Y^2$ and $Y^3$ are, independently, O, S, N;
B is a single bond or a double bond;
A and Z are, independently, $C_{1-6}$ alkyl;
$R^1$ is $CF_3$ or $CF_2H$;
$R^{2b}$ and $R^{3b}$ are, independently, $C_1$-$C_8$ alkyl, wherein $R^{2b}$ and $R^{3b}$ are optionally joined to form a 5-8 membered ring;
$R^{4b}$ and $R^{5b}$ are, independently, $C_1$-$C_8$ alkyl; and
$R^{18}$ and $R^{19}$ are, independently, hydrogen or $C_1$-$C_6$ alkyl;
comprising the step of reacting a compound of formula XXIA:

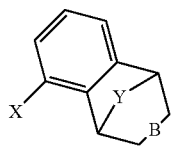

(XXIA)

wherein
X is F, Cl, Br, I or a sulphonate;
B is a single bond or a double bond; and
Y is as defined for the compound of formula XXA;
with a compound of formula XXIIA:

(XXIIA)

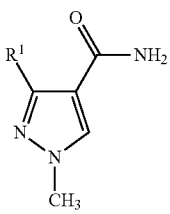

wherein $R^1$ is $CF_3$ or $CF_2H$.

The following sets out preferred substituent definitions of the above substituents which may be combined in any combination.
Preferably, A and Z are each, independently, $C_1$-$C_4$ alkyl.
Preferably, A and Z are each, independently, $CH_3$.
Preferably Y is $CHCHR^{18}(R^{19})$ or $C=C(A)Z$.
Preferably Y is $CHCH(CH_3)CH_3$ or $C=C(CH_3)CH_3$.
Preferably Y is $CHCH(CH_3)CH_3$.
Preferably, $Y^2$ and $Y^3$ are each, independently, O or S.
Preferably, $Y^2$ and $Y^3$ are each O.

Preferably B is a single bond.
Preferably, $R^1$ is $CF_3$, $CHF_2$ or $CH_2F$.
Preferably, $R^1$ is $CF_3$ or $CHF_2$.
Preferably, $R^1$ is $CHF_2$.
Preferably m is 0 and n is 0.
Preferably $R^{2b}$ and $R^{3b}$ are each, independently, $C_{1-4}$ alkyl; or $R^2$ and $R^3$ are together a 4-6 membered ring.
Preferably, $R^{2b}$ and $R^{3b}$ are each, independently, methyl or ethyl; or $R^{2b}$ and $R^{3b}$ are together an ethylene or propylene group.
Preferably, $R^{2b}$ and $R^{3b}$ are each, independently, methyl or $R^{2b}$ and $R^{3b}$ are together an ethylene group.
Preferably, $R^{4b}$ and $R^{5b}$ are each, independently, $C_{1-4}$ alkyl.
Preferably, $R^{4b}$ and $R^{5b}$ are each, independently, methyl or ethyl, preferably methyl.
Preferably, $R^{12}$ and $R^{13}$ are each, independently, hydrogen, $C_1$-$C_4$ alkyl or $C_1$-$C_4$ alkoxy.
Preferably, $R^{12}$ and $R^{13}$ are each, independently, hydrogen or $C_1$-$C_4$ alkyl.
Preferably, $R^{12}$ is hydrogen and $R^{13}$ is $C_1$-$C_4$ alkyl.
Preferably, $R^{12}$ is hydrogen and $R^{13}$ is $CH(CH_3)CH_3$.
Preferably $R^{18}$ is methyl or ethyl.
Preferably $R^{19}$ is methyl.

In a further embodiment the invention relates to a reaction comprising preparing a compound of formula XXX (compound XXX is Isopyrazam):

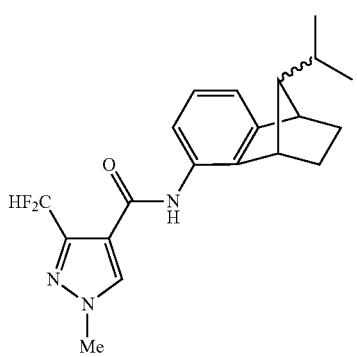

(XXX)

comprising the step of reacting a compound of formula XXXI:

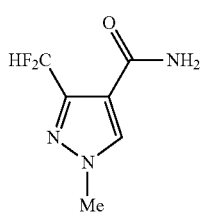

(XXXI)

with a compound of formula XXXII:

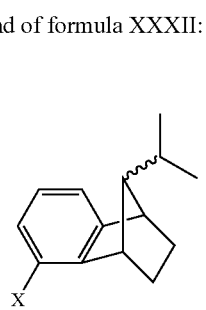

(XXXII)

wherein X is halogen or a sulphonate, preferably Cl.

In a further embodiment the invention relates to a reaction comprising preparing a compound of formula XXXV:

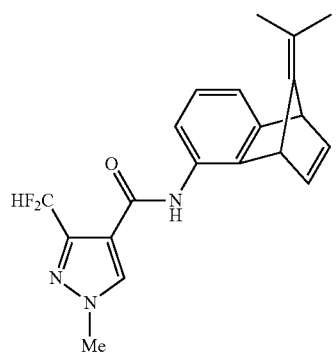

(XXXV)

comprising the step of reacting a compound of formula XXXI:

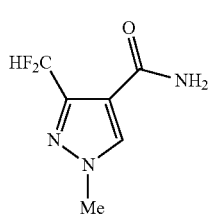

(XXXI)

with a compound of formula XXXVI:

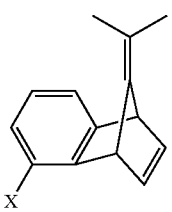

(XXXVI)

wherein X is halogen or a sulphonate, preferably Cl.

In a further embodiment the invention relates to a reaction comprising preparing a compound of formula XXXVII:

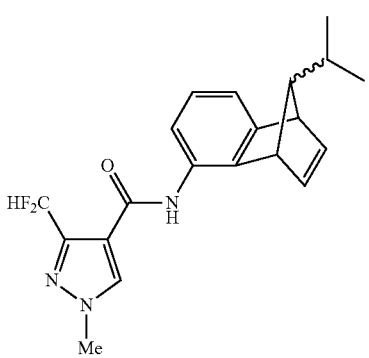

(XXXVII)

comprising the step of reacting a compound of formula XXXI:

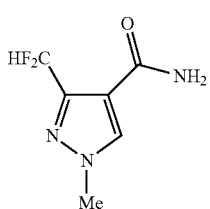
(XXXI)

with a compound of formula XXXIII

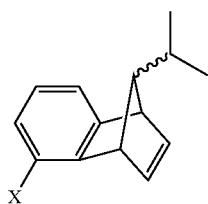
(XXXIII)

wherein X is halogen or a sulphonate, preferably Cl.

In a further embodiment the invention relates to a reaction comprising preparing a compound of formula XXXX:

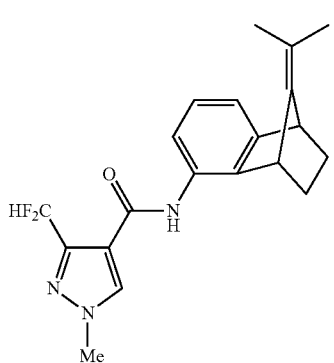
(XXXX)

comprising the step of reacting a compound of formula XXXI:

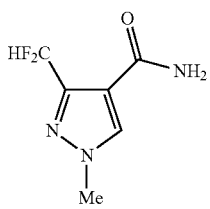
(XXXI)

with a compound of formula XXXXI:

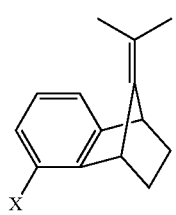
(XXXXI)

wherein X is halogen or a sulphonate, preferably Cl.

In a further embodiment the invention relates to a reaction comprising preparing a compound of formula XXXXVII:

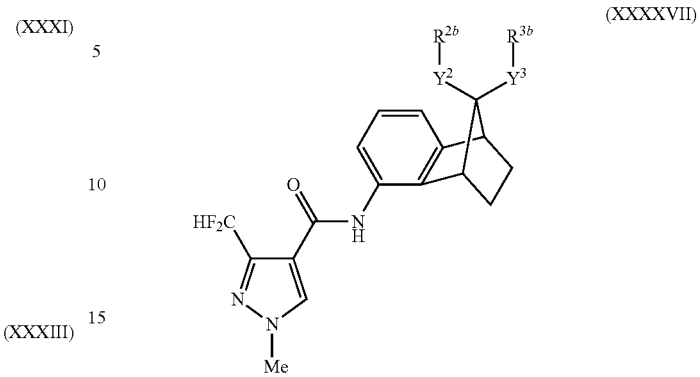
(XXXXVII)

wherein
$Y^2$ and $Y^3$ are independently O, S, N;
$R^{2b}$ and $R^{3b}$ are independently $C_{1-6}$ alkyl, wherein $R^{2b}$ and $R^{3b}$ are optionally joined to form a 5-8 membered ring;
comprising the step of reacting a compound of formula XXXXIV:

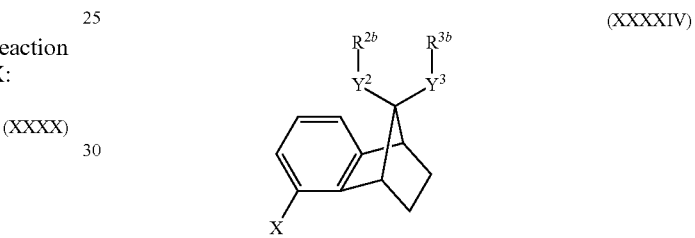
(XXXXIV)

wherein
$Y^2, Y^3, R^{2b}$ and $R^{3b}$ are as defined for formula XXXXVII;
X is F, Cl, Br, I, or a sulphonate, preferably Cl;
with a compound of formula XXXI:

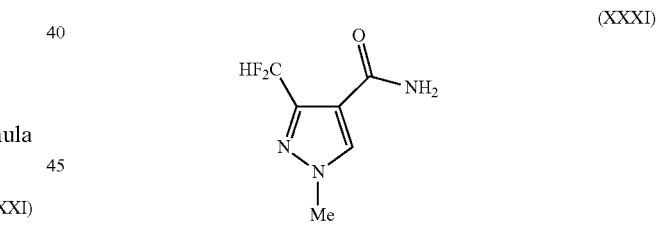
(XXXI)

In a further embodiment the invention relates to a reaction comprising preparing a compound of formula XXXXVIII:

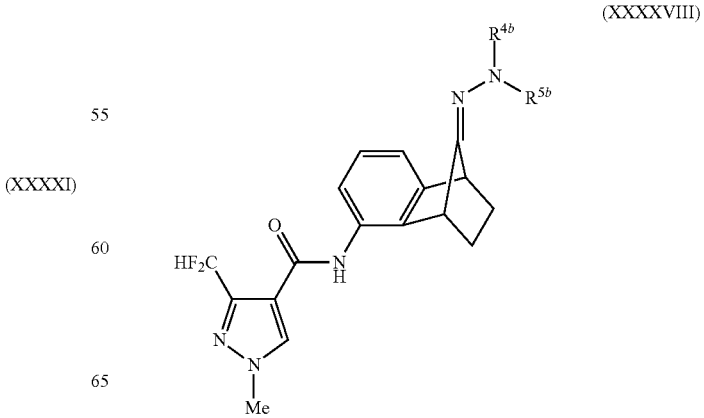
(XXXXVIII)

wherein
R$^{4b}$ and R$^{5b}$ are independently C$_{1-8}$ alkyl;
comprising the step of reacting a compound of formula XXXXV:

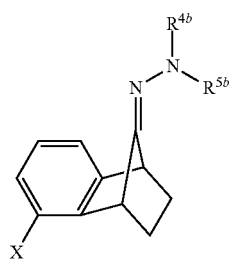

(XXXXV)

wherein
X is halogen or a sulphonate, preferably Cl;
R$^{4b}$ and R$^{5b}$ are independently C$_{1-8}$ alkyl;
with a compound of formula XXXI:

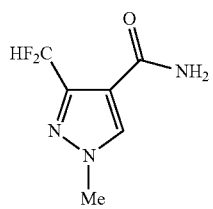

(XXXI)

The invention also relates to a reaction comprising preparing a compound of formula XXXXIX (compound XXXXIX is Sedaxane):

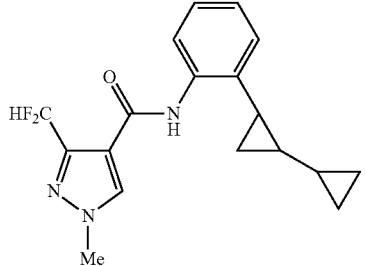

(XXXXIX)

comprising the step of reacting a compound of formula XXXI:

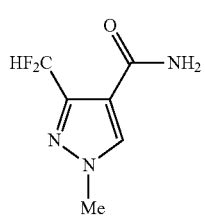

(XXXI)

with a compound of formula L:

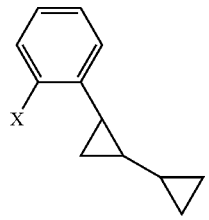

(L)

wherein X is halogen or a sulphonate, preferably Cl.

The invention also relates to a reaction comprising preparing a compound of formula LI (compound of formula LI is Bixafen):

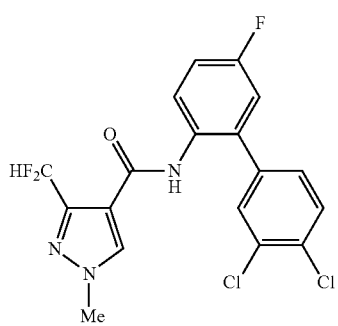

(LI)

comprising the step of reacting a compound of formula XXXI:

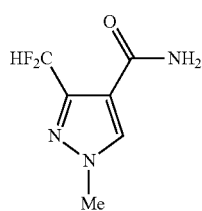

(XXXI)

with a compound of formula LII:

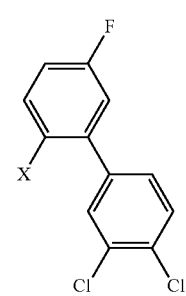

(LII)

wherein X is halogen or a sulphonate, preferably Cl.

The invention also relates to a reaction comprising preparing a compound of formula LV (compound LV is Penthiopyrad):

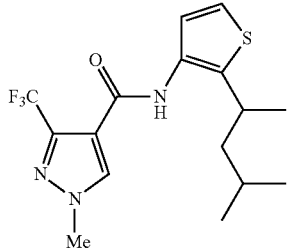
(LV)

comprising the step of reacting a compound of formula XXXI:

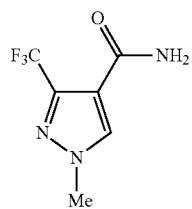
(LVI)

with a compound of formula LVII:

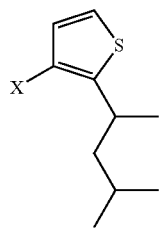
(LVII)

wherein X is halogen or a sulphonate, preferably Cl.

The invention also relates to a reaction comprising preparing a compound of formula LX (compound LX is Penflufen):

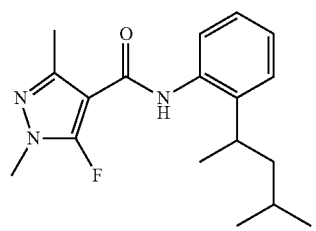
(LX)

comprising the step of reacting a compound of formula LXI:

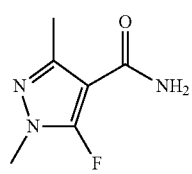
(LXI)

with a compound of formula LXII:

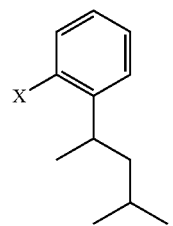
(LXII)

wherein X is halogen or a sulphonate, preferably Cl.

The invention also relates to a reaction comprising preparing a compound of formula LXV:

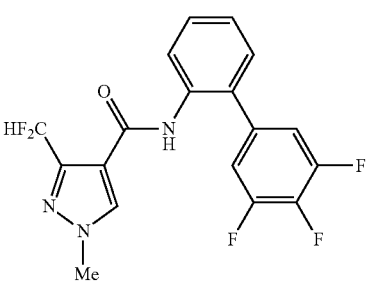
(LXV)

comprising the step of reacting a compound of formula XXXI:

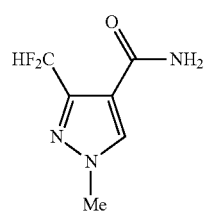
(XXXI)

with a compound of formula LXVI:

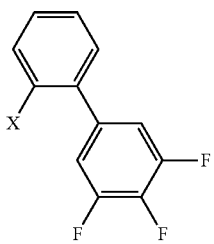
(LXVI)

wherein X is halogen or a sulphonate, preferably Cl.

In a further aspect of the invention there is provided a method comprising
i. preparing a compound of formula XXXXII:

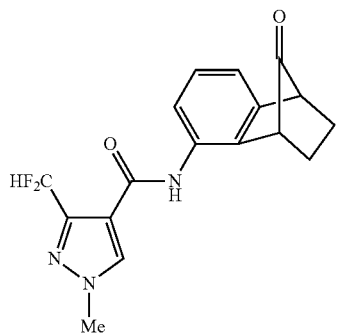
(XXXXII)

comprising the steps of:
(a) protecting the ketone group in the compound of formula XXXXIII:

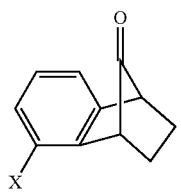
(XXXXIII)

wherein X is F, Cl, Br, I, or a sulphonate, preferably Cl;
using a suitable protecting reagent;
(b) reacting the compound produced in step (a) with a compound of formula XXXI:

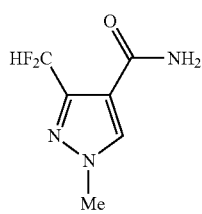
(XXXI)

in the presence of a catalyst, which catalyst comprises copper and a ligand; and
(c) deprotecting the ketone.

Suitable protecting groups will be apparent to the skilled person and include, for example, alcohols, such as 1,2 alcohols, thiols, such as 1,2 thiols, amines, such as 1,2 amines and hydrazines.

For example, the product of step (a) may be a compound of formula XXXXIV or XXXXV:

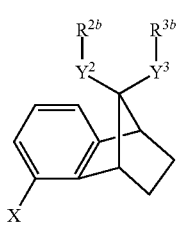
(XXXXIV)

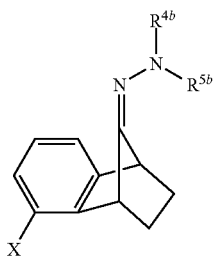
(XXXXV)

wherein
$Y^2$ and $Y^3$ are independently O, S, N;
$R^{2b}$ and $R^{3b}$ are independently $C_{1-8}$ alkyl, wherein $R^{2b}$ and $R^{3b}$ are optionally joined to form a 5-8 membered ring;
$R^{4b}$ and $R^{5b}$ are independently $C_{1-8}$ alkyl;
X is F, Cl, Br, I, or a sulphonate, preferably Cl.

For example, the product of step (b) may be the a compound of formula (XXXXVII) or a compound of formula (XXXXVIII).

The method may comprise
ii. optionally converting the compound of formula XXXXII:

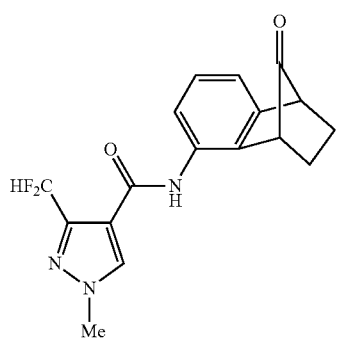
(XXXXII)

to a compound of formula XXXXVI:

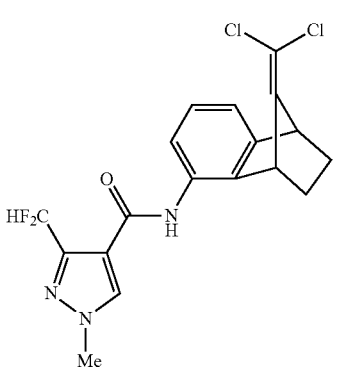
(XXXXVI)

e.g. by reacting the compound of formula (XXXXII) with a suitable reagent such as triphenylphosphine and carbon tetrachloride.

The invention also includes compounds of the formula LI, LVII, and LXVI, in which X is halogen or sulphonate, preferably chlorine.

The present invention also relates to compounds of the formula XXXXIII, XXXXIV, XXXXV, XXXXI, XXXIII, XXXXVII, XXXXVIII:

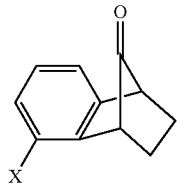
(XXXXIII)

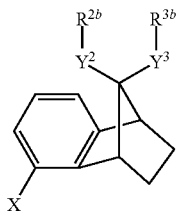
(XXXXIV)

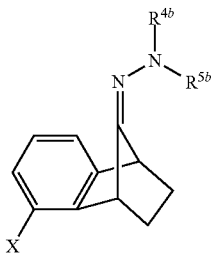
(XXXXV)

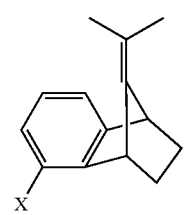
(XXXXI)

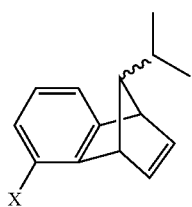
(XXXXIII)

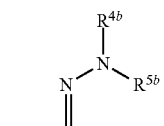
(XXXXVII)

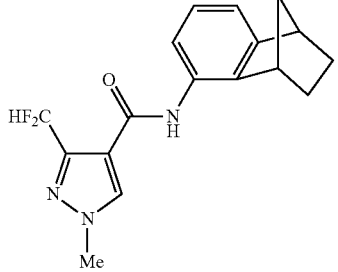

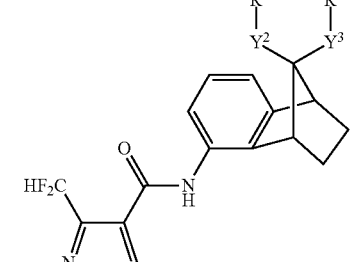
(XXXXVIII)

wherein
$Y^2$ and $Y^3$ are independently O, S, N;
$R^{2b}$ and $R^{3b}$ are independently $C_1$-$C_8$-alkyl, wherein $R^{2b}$ and $R^{3b}$ are optionally joined to form a 5-8 membered ring;
$R^{4b}$ and $R^{5b}$ are independently $C_1$-$C_8$-alkyl;
X is F, Cl, Br, I, or a sulphonate;
excluding the compounds of formula XXXXVIII:
  i. $Y^2$ is O, $Y^3$ is O, $R^{2b}$ is $C_3H_7$-(n), $R^{3b}$ is $C_3H_7$-(n);
  ii. $Y^2$ is O, $Y^3$ is O, $R^{2b}$ is $C_2H_5$, $R^{3b}$ is $C_2H_5$;
  iii. $Y^2$ is O, $Y^3$ is O, $R^{2b}$ and $R^{3b}$ are together —$CH_2$—$CH_2$—.
  Preferably, X is Cl.

Generally, compounds of formula III may be prepared from the corresponding acid chlorides, for example, according to the following scheme:

Scheme 2

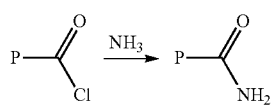

Aqueous or gaseous ammonia may be used, or an ammonium salt, such as ammonium acetate. Suitable solvents, e.g. THF, and reaction conditions may be selected by the person skilled in the art. The acid chloride may be prepared as described, for example, in WO 04/035589. Alternatively, the amide may be prepared by reacting ammonia with the ester of the corresponding heterocycle.

Compounds of formula X and XII may be prepared using the methodology described in WO 04/035589, and WO 2007/068417, for example. Compounds of formula (XXXII) may be prepared according to the following scheme:

Scheme 3

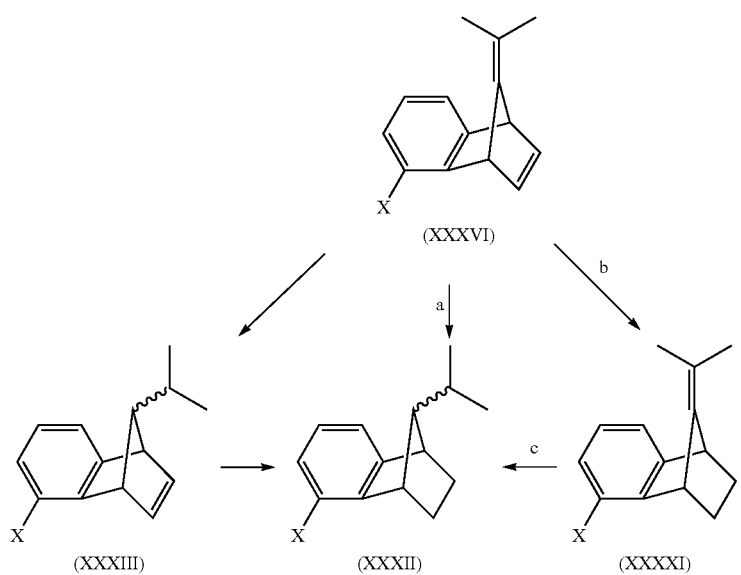

The compounds of formula XXXVI, XXXII and XXXVI may be prepared using methodology as described in WO 2007/068417. Reactions a and c may be performed as described in WO 2007/068417, e.g. using a hydrogenation catalyst such as 5% Pd/C, 5% Raney Nickel, or 5% Rhodium on carbon, in a solvent such as methanol, ethanol, THF or ethyl acetate. Reactions b may also be performed using the methodology described in WO 2007/068417 for the corresponding nitro/amine substituted norbornenes. The extent of hydrogenation may also be controlled e.g. by using Wilkinson's catalyst (RhCl(PPh$_3$)$_3$). Compound XXXIII may be produced during the course of reaction a or b. The compounds may be isolated according to known procedures, e.g. HPLC.

Penthiopyrad is described in EP0737682. Bixafen is described in EP1490342. Sedaxane is described in WO 03/074491; Isopyrazam is described in WO 02/083858; Penflufen is described in WO 2008/006575.

The present invention will now be described by way of the following non-limiting examples. Those skilled in the art will promptly recognize appropriate variations from the procedures both as to reactants and as to reaction conditions and techniques.

All references mentioned herein are incorporated by reference in their entirety. All aspects and preferred features of the invention may be combined with each other, except where this is evidently not possible.

FIGURES

FIG. 1—FIG. 1 shows the reaction profile in terms of percent conversion of reactants to products when (i) all reactants are included at the start of the reaction (ii) the ligand is added last, and (iii) the amide is added last. The reaction is described in Example 6 and relates to Amidation of 4-Chlorotoluene with 3-Difluoromethyl-1-methyl-1H-pyrazole-4-carboxylic acid amide.

Figure 2:
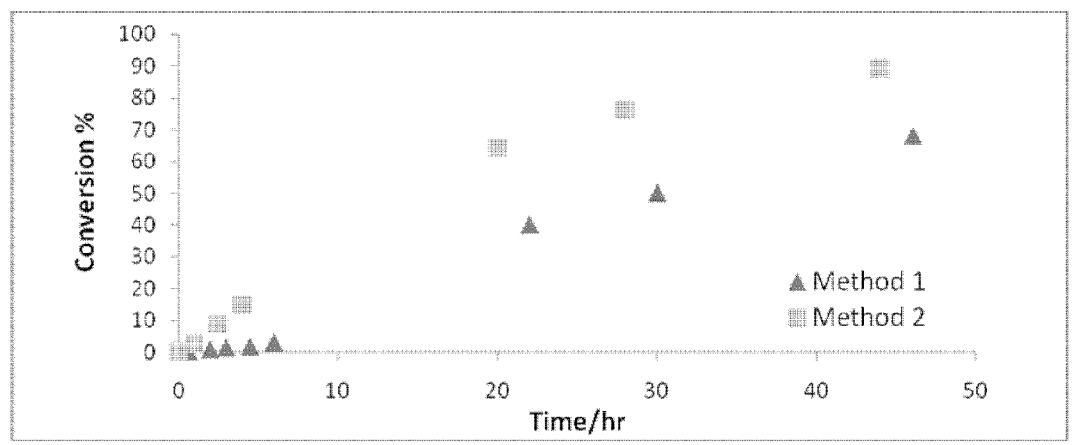

FIG. 2—FIG. 2 shows the reaction profile in terms of percent conversion of reactants to products when (i) all reactants are included at the start of the reaction (method 1) and (ii) when ligand is added after dissolving the amide (method 2). The reaction is described in Example 7 and relates to Amidation of 4-Chlorotoluene with Benzamide.

EXAMPLES

Example 1

Amidation of 5-Chloro-9-isopropyl-1,2,3,4-tetrahydro-1,4-methano-naphthalene with 3-Difluoromethyl-1-methyl-1H-pyrazole-4-carboxylic acid amide which was partially dissolved before addition of N,N'-Dimethyl-trans-1,2-cyclohexanediamine/CuBr catalyst

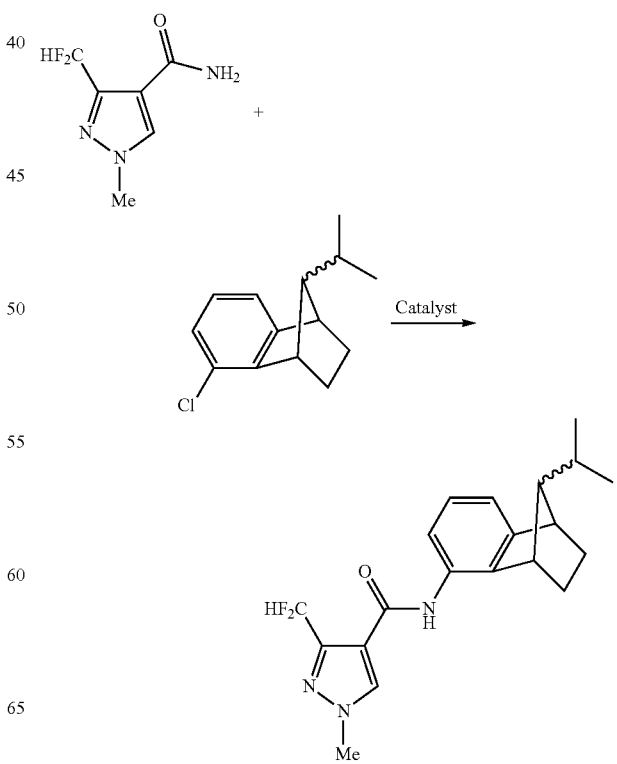

An oven-dried multi-necked flask was evacuated and refilled with nitrogen three times. 3-Difluoromethyl-1-methyl-1H-pyrazole-4-carboxylic acid amide (1.75 g, 10 mmol), 5-Chloro-9-isopropyl-1,2,3,4-tetrahydro-1,4-methano-naphthalene (2.20 g, 10 mmol), potassium carbonate (0.77 g, 5.5 mmol) and solvent ethylene glycol diethyl ether (5 mL) were charged into the flask, and the flask evacuated and refilled with nitrogen once more. This suspension was heated to 150° C., with stirring, over 20 minutes. Once at temperature, the mixture was stirred for a further two hours, before adding pre-mixed copper I bromide (280 mg, 20 mol %) and N,N'-Dimethylcyclohexanediamine (0.69 mL, 44 mol %) and stirring for a further 12 hours at 150° C., in situ product yield=92%, rest remaining starting materials. The resulting suspension was cooled to room temperature, and a small volume of acetone (1-2 mL) was added to improve the mobility of the suspension. Water with 0.1% $H_3PO_4$ was added to the suspension until solids started to crash out. The resulting suspension was left for 1.5 hours to allow the solid product to crash out of the (blue) aqueous solution. The solid product was filtered off under vacuum, and washed with toluene (5-10 mL), which removed a large amount of the dark colour from the recovered solids. The isolated product yield (not optimised) was 86%.

Example 2

Amidation of 5-Chloro-9-isopropyl-1,2,3,4-tetrahydro-1,4-methano-naphthalene with 3-Difluoromethyl-1-methyl-1H-pyrazole-4-carboxylic acid amide with N,N'-Dimethyl-trans-1,2-cyclohexanediamine/ CuBr catalyst when either 3-Difluoromethyl-1-methyl-1H-pyrazole-4-carboxylic acid amide or 5-Chloro-9-isopropyl-1,2,3,4-tetrahydro-1,4-methano-naphthalene added last An oven-dried multi-necked flask was evacuated and refilled with nitrogen three times. 3-Difluoromethyl-1-methyl-1H-pyrazole-4-carboxylic acid amide (1.75 g, 10 mmol) or 5-Chloro-9-isopropyl-1,2,3,4-tetrahydro-1,4-methano-naphthalene (2.20 g, 10 mmol), with potassium carbonate (0.77 g, 5.5 mmol) and diethylene glycol diethyl ether (5 mL) were charged into the flask, and the flask evacuated and refilled with nitrogen once more. This suspension was heated to 150° C., with stirring, over 20 minutes. Once at temperature, the mixture was stirred for a further two hours, before adding pre-mixed copper I bromide (280 mg, 20 mol %) and N,N'-Dimethylcyclohexanediamine (0.69 mL, 44 mol %) and stirring for a further 1 hour at 150° C. The remaining reagent, aryl chloride, or amide, was added to the reaction mixture and the suspension stirred for a further 12 hours at 150° C. In situ product yield=88% when 5-Chloro-9-isopropyl-1,2,3,4-tetrahydro-1,4-methano-naphthalene added last and 26% when 3-Difluoromethyl-1-methyl-1H-pyrazole-4-carboxylic acid amide added last, the remainder being starting materials.

Example 3

Amidation of 5-Chloro-9-isopropyl-1,2,3,4-tetrahydro-1,4-methano-naphthalene with 3-Difluoromethyl-1-methyl-1H-pyrazole-4-carboxylic acid amide with N,N'-Dimethyl-trans-1,2-cyclohexanediamine/ CuBr catalyst when either CuBr or N,N'-Dimethyl-trans-1,2-cyclohexanediamine added last (i) CuBr Salt Last An oven-dried Schlenk was charged with 3-Difluoromethyl-1-methyl-1H-pyrazole-4-carboxylic acid amide (1.39 g, 8 mmol), 5-Chloro-9-isopropyl-1,2,3,4-tetrahydro-1,4-methano-naphthalene (1.75 g, 8 mmol), potassium carbonate (600 mg, 4.4 mmol), evacuated and back filled with nitrogen 3 times. Diglyme (4 mL) was added and the mixture was stirred magnetically under nitrogen at 150° C. for two hours. N,N'-Dimethyl-trans-1,2-cyclohexanediamine (500 mg, 3.4 mmol, 44 mol %) was then added to the reaction at 150° C. and was allowed to stir for 5 minutes. Solid copper (I) bromide (230 mg, 1.6 mmol, 20 mol %) was then added to the reaction mixture at 150° C. and the resultant deep green/brown reaction was stirred at 150° C. for a further 18 hours. GC analysis after 18 hours indicated 84% conversion.

(ii) N,N'-Dimethyl-trans-1,2-cyclohexanediamine last

An oven-dried Schlenk was charged with 3-Difluoromethyl-1-methyl-1H-pyrazole-4-carboxylic acid amide (1.39 g, 8 mmol), 5-Chloro-9-isopropyl-1,2,3,4-tetrahydro-1,4-methano-naphthalene (1.75 g, 8 mmol), potassium carbonate (600 mg, 4.4 mmol), evacuated and back filled with nitrogen 3 times. Diglyme (4 mL) was added and the mixture was stirred magnetically under nitrogen at 150° C. for two hours. Solid copper (I) bromide (230 mg, 1.6 mmol, 20 mol %) was then added to the reaction at 150° C. and was allowed to stir for 5 minutes to afford a deep orange mixture. N,N'-Dimethyl-trans-1,2-cyclohexanediamine (500 mg, 3.4 mmol, 44 mol %) was then added to the reaction mixture at 150° C. and the resultant deep green/brown reaction was stirred at 150° C. for a further 18 hours. GC analysis after 18 hours indicated 90% conversion.

Example 4

Solvent effect on the Amidation of 5-Chloro-9-isopropyl-1,2,3,4-tetrahydro-1,4-methano-naphthalene with 3-Difluoromethyl-1-methyl-1H-pyrazole-4-carboxylic acid amide The method described in Example 1 was repeated in a range of solvents at different temperatures, see Table 1.

TABLE 1

| Solvent | Temperature/ ° C. | In Situ Yield |
| --- | --- | --- |
| Digylme | 150 | 92% |
| Ethyl diglyme | 180 | 80% |
| DMF | 150 | 98% |
| NMP | 150 | 96% |
| Cyclohexanol | 150 | 88% |
| Cyclohexanone | 150 | 48% (note all starting materials reacted, many side products) |
| Anisole | 140 | 22% |
| Amyl acetate | 130 | 0% |
| Butyl acetate | 120 | 0% |
| 1,4-Dioxane | 100 | 0% |
| Ethyl acetate | 70 | 0% |
| 4-Fluorotoluene | 100 | 0% |
| Toluene | 120 | 0% |

Example 5

Amidation of 5-Chloro-9-isopropyl-1,2,3,4-tetrahydro-1,4-methano-naphthalene with 3-Difluoromethyl-1-methyl-1H-pyrazole-4-carboxylic acid amide using N,N'-Dimethylethylenediamine as ligand An oven-dried multi-necked flask was evacuated and refilled with nitrogen three times. 3-Difluoromethyl-1-methyl-1H-pyrazole-4-carboxylic acid amide (1.75 g, 10 mmol), 5-Chloro-9-isopropyl-1,2,3,4-tetrahydro-1,4-methano-naphthalene (2.20 g, 10 mmol), potassium carbonate (0.77 g, 5.5 mmol), copper bromide (280 mg, 20 mol %) and cyclohexanol (5 mL) were charged into the flask, and the flask evacuated and refilled with nitrogen once more. This suspension was heated to 150° C., with stirring, over 20 minutes. Once at temperature, the mixture was stirred for a further two hours, before adding N,N'-Dimethylethylenediamine (0.47 mL, 44 mol %) subsurface and stirring for a further 12 hours at 150° C. The in situ product yield was 88%, The remainder being starting materials. Repeating in a sealed tube to avoid loss of the volatile ligand resulted in a much faster reaction and 78% conversion after only 5 hours, the remainder being starting materials.

Example 6

Effect of the addition order on the Amidation of 4-Chlorotoluene with 3-Difluoromethyl-1-methyl-1H-pyrazole-4-carboxylic acid amide

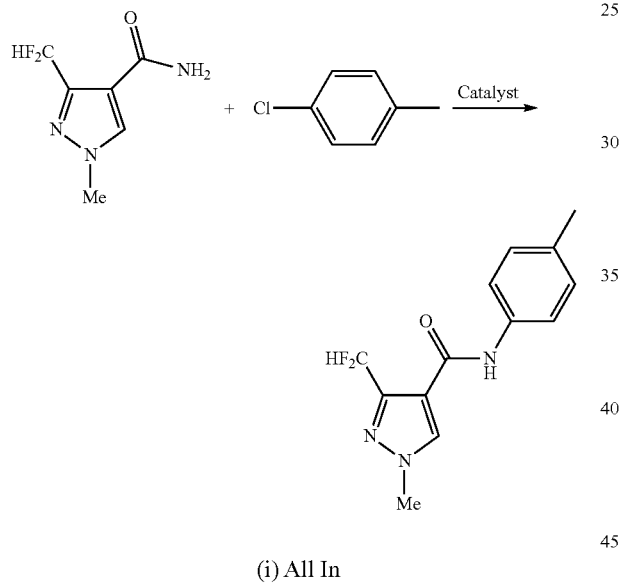

(i) All In

An oven-dried Schlenk was charged with Difluoromethyl-1-methyl-1H-pyrazole-4-carboxylic acid amide (723 mg, 4 mmol), 4-chlorotoluene (2 mL, 17 mmol), K$_2$CO$_3$ (1.2 g, 8.7 mmol), Solid copper (I) bromide (60 mg, 0.21 mmol, 11 mol %) evacuated and back filled with nitrogen 3 times. Diglyme (4 mL) and N,N'-Dimethyl-trans-1,2-cyclohexanediamine (70 uL, 0.44 mmol, 22 mol %) was then added and the mixture was stirred magnetically under nitrogen at 140° C. with periodic sampling.

(ii) N,N'-Dimethyl-trans-1,2-cyclohexanediamine added last

An oven-dried Schlenk was charged with Difluoromethyl-1-methyl-1H-pyrazole-4-carboxylic acid amide (723 mg, 4 mmol), 4-chlorotoluene (2 mL, 17 mmol), K$_2$CO$_3$ (1.2 g, 8.7 mmol), Solid copper (I) bromide (60 mg, 0.21 mmol, 11 mol %) evacuated and back filled with nitrogen 3 times. Diglyme (4 mL) and was then added and the mixture was stirred magnetically under nitrogen at 140° C. for two hours. N,N'-Dimethyl-trans-1,2-cyclohexanediamine (70 uL, 0.44 mmol, 22 mol %) was then added and the resultant deep green/brown reaction was stirred at 140° C. with periodic sampling.

(iii) Difluoromethyl-1-methyl-1H-pyrazole-4-carboxylic acid amide added last

An oven-dried Schlenk was charged with 4-chlorotoluene (2 mL, 17 mmol), K$_2$CO$_3$ (1.2 g, 8.7 mmol), Solid copper (I) bromide (60 mg, 0.21 mmol, 11 mol %), N,N'-Dimethyl-trans-1,2-cyclohexanediamine (70 uL, 0.44 mmol, 22 mol %) evacuated and back filled with nitrogen 3 times. Diglyme (4 mL) was then added and the mixture was stirred magnetically under nitrogen at 140° C. for 2 hours. Difluoromethyl-1-methyl-1H-pyrazole-4-carboxylic acid amide (723 mg, 4 mmol) was then added and the resultant brown reaction was stirred at 140° C. with periodic sampling.

Results

The results are shown in Table 2.

TABLE 2

| Time (hours) | Conversion |
| --- | --- |
| Reaction (i) - All In | |
| 0.5 | 13% |
| 1 | 18% |
| 2 | 29% |
| 3.5 | 36% |
| 4.5 | 61% |
| 5.5 | 69% |
| Reaction (ii) - N,N'-Dimethyl-trans-1,2-cyclohexanediamine last | |
| 0.5 | 23% |
| 1 | 38% |
| 2 | 53% |
| 3.5 | 79% |
| 4.5 | 85% |
| 5.5 | 91% |
| Reaction (iii) - 1-methyl-3-difluoromethyl-1H-pyrazole-4-carboxylic acid amine last | |
| 0.5 | 8% |
| 1 | 11% |
| 2 | 9% |
| 3.5 | 13% |
| 4.5 | 20% |
| 5.5 | 25% |

Example 7

Effect of Addition Order on the Amidation of 4-Chlorotoluene with Benzamide

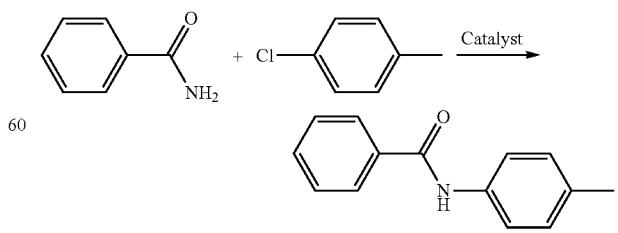

Method 1: A dried flask was evacuated and refilled with nitrogen, and then charged with benzamide (1.2 g, 10 mmol), chlorotoluene (1.27 g, 10 mmol), CuBr (0.14 g, 10 mol %), potassium carbonate (1.7 g, 12 mmol), N,N'-Dimethylcyclohexanediamine (0.2 mL, 22 mol %) and diglyme (4 mL). The resulting suspension was heated to 150° C. over 15 minutes and stirred over two nights at 150° C. with sampling.

Method 2: A dried flask was evacuated and refilled with nitrogen, and then charged with benzamide (1.2 g, 10 mmol), chlorotoluene (1.27 g, 10 mmol), CuBr (0.14 g, 10 mol %), potassium carbonate (1.7 g, 12 mmol) and diglyme (4 mL). The suspension was heated to 150° C. over 15 minutes, and held at this temperature for two hours before adding N,N'-Dimethylcyclohexanediamine (0.2 mL, 22 mol %). The resulting suspension was stirred over two nights at 150° C. with sampling.

Results

The results are shown in Table 3.

TABLE 3

| Time (hours) | Method 1 (conversion %) | Method 2 (conversion %) |
|---|---|---|
| 0 | 0 | 0 |
| 0.67 | 0 | |
| 1 | | 2.5 |
| 2 | 0.7 | |
| 2.5 | | 8.7 |
| 3 | 1.3 | |
| 4 | | 15 |
| 4.5 | 1.7 | |
| 6 | 3 | |
| 20 | | 64 |
| 22 | 40 | |
| 28 | | 76 |
| 30 | 50 | |
| 44 | | 89 |
| 46 | 68 | |

Example 8

Amidation of 5-Chloro-9-isopropyl-1,2,3,4-tetrahydro-1,4-methano-naphthalene with 3-Difluoromethyl-1-methyl-1H-pyrazole-4-carboxylic acid amide with N,N'-Dimethyl-trans-1,2-cyclohexanediamine/CuBr catalyst 5-Chloro-9-isopropyl-1,2,3,4-tetrahydro-1,4-methano-naphthalene (2.2 g, 10 mmol) was weighed into a round bottomed flask and heated with stirring, allowing it to fully melt. 1-Methyl-3-difluoromethyl-1H-pyrazole-4-caroxylic acid amide (0.44 g, 2.5 mmol), and K$_2$CO$_3$ (0.2 g, 1.4 mmol) were then added, and the suspension allowed to heat to 150° C., and kept at this temperature for two hours. Copper bromide (70 mg, 20 mol %) and N,N'-Dimethylethylenediamine (0.12 mL, 44 mol %) were then added to the suspension and the reaction stirred overnight at 150° C. under a slight positive pressure of nitrogen. After this time, a sample was removed from the reaction for analysis by HPLC. Conversion as measured by HPLC was 89% (based on DFP-amide).

Example 9

Amidation of 5-Chloro-9-isopropyl-1,2,3,4-tetrahydro-1,4-methano-naphthalene with 3-Difluoromethyl-1-methyl-1H-pyrazole-4-carboxylic acid amide with N1-methyl-propane-1,3-diamine/CuBr catalyst An oven dried flask was evacuated and refilled with nitrogen three times before adding 5-Chloro-9-isopropyl-1,2,3,4-tetrahydro-1,4-methano-naphthalene (2.20 g, 10 mmol), 1-Methyl-3-difluoromethyl-1H-pyrazole-4-caroxylic acid amide (1.75 g, 10 mmol), potassium carbonate (0.8 g, 5.7 mmol), and CuBr (280 mg, 20 mol %) and diglyme (5 mL). The suspension was heated with stirring to 150° C., and allowed to stir at this temperature for 2 hours prior to adding ligand N1-methyl-propane-1,3-diamine (0.31 mL, 44 mol %) and stirring at 150° C. overnight. After this time, a sample was removed for analysis by HPLC. Conversion was 64% as measured by HPLC.

Example 10

Preparation of 3-Difluoromethyl-1-methyl-1H-pyrazole-4-carboxylic acid (9-dichloromethylene-1,2,3,4-tetrahydro-1,4-methano-naphthalen-5-yl)-amide (a) Preparation of 5-Chloro-9,9-dimethoxy-1,2,3,4-tetrahydro-1,4-methano-naphthalene (compound 2)

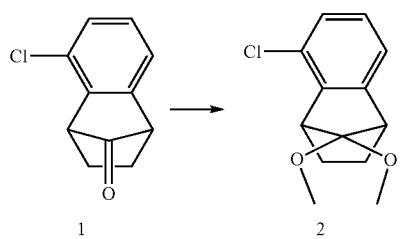 [SMILES: O=C1C2CCC1c1c(Cl)cccc12 ; COC1(OC)C2CCC1c1c(Cl)cccc12]

An oven-dried 50 mL 3-neck flask was charged with compound 1 (4 g, 20.8 mmol), trimethyl orthoformate (2.9 mL, 28.2 mmol) followed by methanol 5 mL under nitrogen and the mixture was stirred at 60° C. Sulfuric acid (200 uL, 50% w/v) was then added dropwise and the mixture was stirred for 20 minutes. Low levels of product precipitation were evident after 10 minutes (white solid). The reaction mixture was cooled at 0° C. for 20 and the precipitate is collected via vacuum filtration and washed with cold methanol (10 mL) to afford compound 2 as a white solid in 95% yield (4.7 g). Residual starting material can be recovered via extraction of the filtrate into diethyl ether followed by concentration in vacuo (150 mg, 4%).

Other potential protecting group are for example:

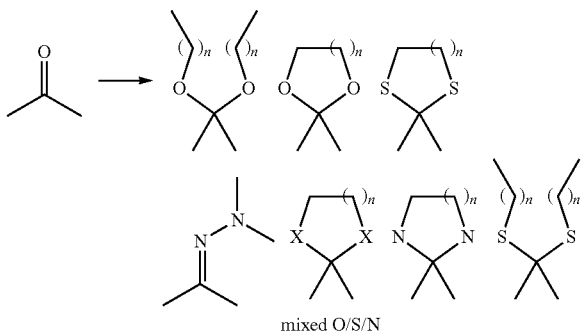

in which n is for example 1 to 4.

(b) Preparation of 3-Difluoromethyl-1-methyl-1H-pyrazole-4-carboxylic acid (9,9-dimethoxy-1,2,3,4-tetrahydro-1,4-methano-naphthalen-5-yl)-amide (compound 4)

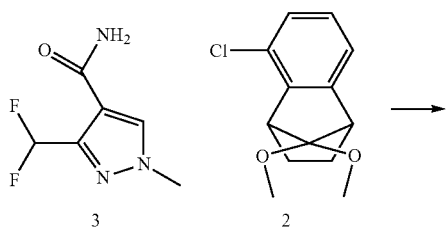

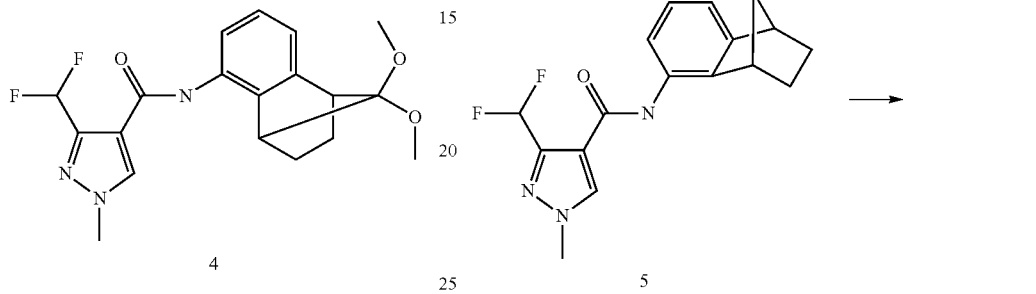

An oven-dried Schlenk was charged with compound 3 (1.39 g, 8 mmol), compound 2 (1.89 g, 8 mmol), K₂CO₃ (600 mg, 4.4 mmol), evacuated and back filled with nitrogen 3 times.

Diglyme (4 mL) was added and the mixture was stirred magnetically under nitrogen at 150° C. for two hours. Solid copper (I) bromide (230 mg, 1.6 mmol, 20 mol %) was then added to the reaction mixture at 150° C. followed by N,N'-Dimethyl-trans-1,2-cyclohexanediamine (500 mg, 3.4 mmol, 44 mol %). The resultant deep green/brown reaction was stirred at 150° C. for a further 18 hours. GC analysis after 18 hours indicated 81% conversion to compound 4.

(c) Preparation of 3-Difluoromethyl-1-methyl-1H-pyrazole-4-carboxylic acid (9-oxo-1,2,3,4-tetrahydro-1,4-methano-naphthalen-5-yl)-amide (compound 5)

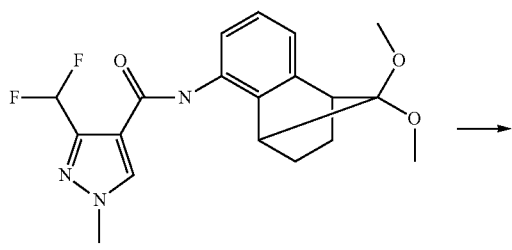

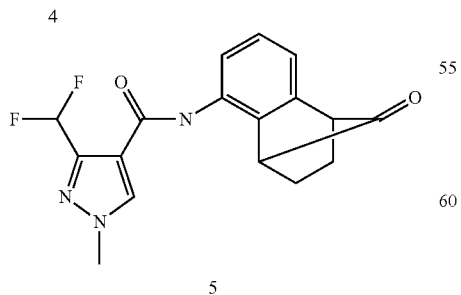

An oven-dried Schlenk was charged with compound 4 (100 mg, 0.26 mmol) and dissolved in acetone (1 mL). Hydrochloric acid was added (37%, 2 drops) and the mixture was stirred under nitrogen for 30 minutes at 50° C. GCMS analysis indicated compete conversion of starting material and water was added to mixture (5 mL). Extraction into ethyl acetate (3×5 mL) followed by concentration in vacuo affords compound 5 (quantitative conversion).

(d) Preparation of 3-Difluoromethyl-1-methyl-1H-pyrazole-4-carboxylic acid (9-dichloromethylene-1,2,3,4-tetrahydro-1,4-methano-naphthalen-5-yl)-amide (compound 6)

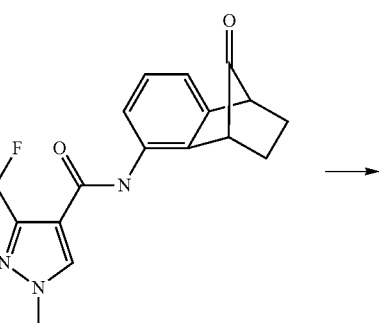

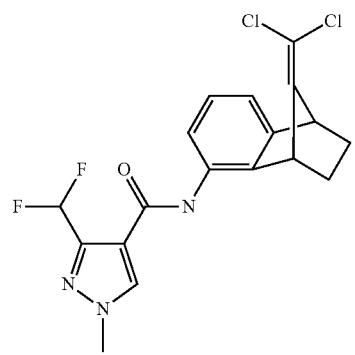

A suspension of compound 5 (400 mg, 1.2 mmol) and triphenylphosphine (mg, 2.7 mmol 2.2 eq) in acetonitrile (2.5 mL) was stirred at room temperature. Carbon tetrachloride (mg, mmol, eq) was then added dropwise over 5 minutes. The reaction mixture was then stirred at 60° C. and quickly became a deep orange solution. After 6 hours the reaction was stopped and cooled to room temperature (adjudged complete via GCMS). The chemical yield of compound 6 in this step was calculated as 76%.

Anyone skilled in the art will readily appreciate that Examples 10a, 10b and 10c can readily be telescoped into a single stage with protection/deprotection done in situ.

The invention claimed is:
1. A method of initiating a reaction represented by scheme 1:

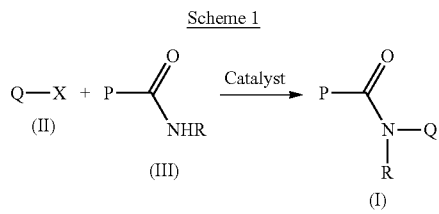

Scheme 1 wherein
Q is phenyl or 5-6 membered heteroaryl containing 1 or 2 heteroatoms independently selected from O, N and S, wherein the phenyl and heteroaryl are optionally substituted by one or more groups independently selected from halogen, $C_1$-$C_8$-alkyl, $C_1$-$C_8$-haloalkyl, $C_1$-$C_8$-alkoxy, cyano, hydroxyl, and amino; and wherein, in addition to the foregoing, the phenyl or heteroaryl is substituted at the ortho position with respect to X by a group selected from phenyl, $C_1$-$C_8$-alkyl, $C_1$-$C_8$-alkoxy, or $C_3$-$C_6$-cycloalkyl, and wherein each phenyl, $C_1$-$C_8$-alkyl, $C_1$-$C_8$-alkoxy, and $C_3$-$C_6$-cycloalkyl is optionally substituted by one or more groups independently selected from halogen, $C_1$-$C_8$-alkyl, $C_1$-$C_8$-alkoxy, $C_3$-$C_6$-cycloalkyl, $C_1$-$C_8$-haloalkyl, $C_1$-$C_8$-haloalkoxy, and $C_3$-$C_6$-halocycloalkyl; or when Q is phenyl it is substituted at the ortho- and meta-position with respect to X by a fused bicyclo[2.2.1]heptane or bicyclo[2.2.1]heptene ring, each optionally substituted with one or more groups independently selected from halogen, $C_1$-$C_8$-alkyl, $C_1$-$C_8$-haloalkyl, $C_1$-$C_8$-alkoxyl, $C_1$-$C_8$-alkylthio, $C_1$-$C_8$-alkylamino, cyano, and hydroxyl, wherein any alkyl, haloalkyl, alkoxy, alkylthio, or alkylamino substituent may join with another alkyl, haloalkyl, alkoxy, alkylthio, or alkylamino substituent to form a ring; or the fused bicyclo[2.2.1]heptane or bicyclo[2.2.1]heptene ring is optionally substituted by =N—N($R^{4b}$)$R^{5b}$, wherein $R^{4b}$ and $R^{5b}$ are independently selected from $C_1$-$C_8$-alkyl; or the fused bicyclo[2.2.1]heptane or bicyclo[2.2.1]heptene ring is optionally substituted by =C($R^{3a}$)$R^{4a}$ wherein $R^{3a}$ and $R^{4a}$ are independently selected from $C_1$-$C_8$ alkyl and $C_1$-$C_8$ haloalkyl;

X is halogen or a sulphonate;
P is phenyl, pyridyl, pyrrole, or pyrazole, each optionally substituted with one to three substituents independently selected from $C_1$-$C_4$-alkyl, $C_1$-$C_4$-haloalkyl and halogen;
R is hydrogen or methyl;
wherein the catalyst comprises copper and a ligand, wherein the ligand is an optionally substituted 1,2 diamine or an optionally substituted 1,3 diamine;
comprising
providing the compound of formula III in liquid form prior to contacting the compound of formula III with the catalyst;
comprising the steps
a) providing the compound of formula III in liquid form,
b) contacting the copper with the compound of formula III,
c) contacting the ligand with the compound of formula III,
wherein at least one of steps b) and c) is performed after step a);
wherein step a) comprises heating the compound of formula III.

2. A method of preparing a compound of formula IA comprising performing the reaction represented by scheme 1A:

Scheme 1A

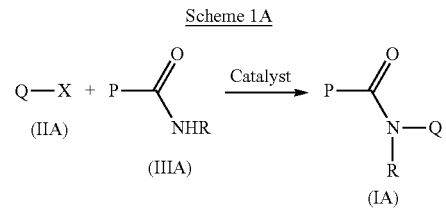

wherein
Q is phenyl or 5-6 membered heteroaryl containing 1 or 2 heteroatoms independently selected from O, N and S, wherein the phenyl and heteroaryl are optionally substituted by one or more groups independently selected from halogen, $C_1$-$C_8$-alkyl, $C_1$-$C_8$-haloalkyl, $C_1$-$C_8$-alkoxy, cyano, hydroxyl, and amino; and wherein, in addition to the foregoing, the phenyl or heteroaryl is substituted at the ortho position with respect to X by a group selected from phenyl, $C_1$-$C_8$-alkyl, $C_1$-$C_8$-alkoxy, or $C_3$-$C_6$-cycloalkyl, and wherein each phenyl, $C_1$-$C_8$-alkyl, $C_1$-$C_8$-alkoxy, and $C_3$-$C_6$-cycloalkyl is optionally substituted by one or more groups independently selected from halogen, $C_1$-$C_8$-alkyl, $C_1$-$C_8$-alkoxyl, $C_3$-$C_6$-cycloalkyl, $C_1$-$C_8$-haloalkyl, $C_1$-$C_8$-haloalkoxy, and $C_3$-$C_6$-halocycloalkyl; or when Q is phenyl it is substituted at the ortho- and meta-position with respect to X by a fused bicyclo[2.2.1]heptane or bicyclo[2.2.1]heptene ring, each optionally substituted with one or more groups independently selected from halogen, $C_1$-$C_8$-alkyl, $C_1$-$C_8$-haloalkyl, $C_1$-$C_8$-alkoxy, $C_1$-$C_8$-alkylthio, $C_1$-$C_8$-alkylamino, cyano, and hydroxyl, wherein any alkyl, haloalkyl, alkoxy, alkylthio, or alkylamino substituent may join with another alkyl, haloalkyl, alkoxy, alkylthio, or alkylamino substituent to form a ring; or the fused bicyclo[2.2.1]heptane or bicyclo[2.2.1]heptene ring is optionally substituted by =N—N($R^{4b}$)$R^{5b}$, wherein $R^{4b}$ and $R^{5b}$ are independently selected from $C_1$-$C_8$-alkyl; or the fused bicyclo[2.2.1]heptane or bicyclo[2.2.1]heptene ring is optionally substituted by =C($R^{3a}$)$R^{4a}$ wherein $R^{3a}$ and $R^{4a}$ are independently selected from $C_1$-$C_8$ alkyl and $C_1$-$C_8$ haloalkyl;

X is halogen or a sulphonate;
P is phenyl, pyridyl, pyrrole, or pyrazole, each optionally substituted with one to three substituents independently selected from $C_1$-$C_4$-alkyl, $C_1$-$C_4$-haloalkyl and halogen;
R is hydrogen or methyl;
wherein the catalyst comprises copper and a ligand, wherein the ligand is an optionally substituted 1,2 diamine or an optionally substituted 1,3 diamine;
wherein the reaction is performed in an organic polar solvent;
comprising the steps:
a) providing the compound of formula IIIA in liquid form,
b) contacting the copper with the compound of formula IIIA,
c) contacting the ligand with the compound of formula IIIA,
wherein at least one of steps b) and c) is performed after step a);

wherein step a) comprises heating the compound of formula IIIA.

3. A method according to claim 1, wherein the compound of formula III is a compound of formula XXII or LXIII:

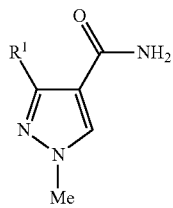

(XXII)

wherein $R^1$ is $CF_3$, $CHF_2$ or $CH_2F$;

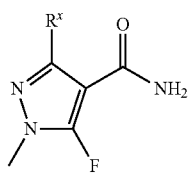

(LXIII)

wherein $R^x$ is selected from $CF_3$, $CHF_2$ and $CH_3$.

4. A method according to claim 1, wherein X is Cl.

5. A method according to claim 1, wherein Q is group V, group VI or group VIIa, group VIIb or group VIIc:

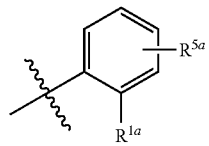

(V)

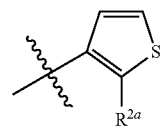

(VI)

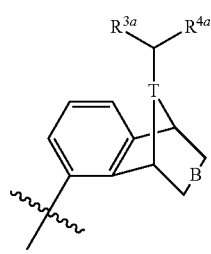

(VIIa)

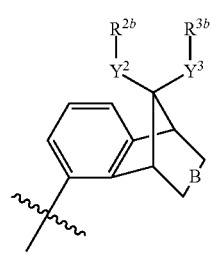

(VIIb)

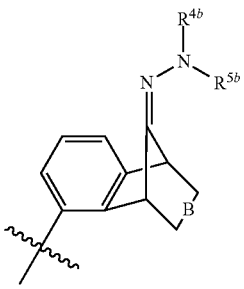

(VIIc)

B is a single or double bond;
T is a single or double bond;
$R^{1a}$ is phenyl optionally substituted with one to three halogen atoms, or $R^{1a}$ is $C_1$-$C_8$-alkyl, $C_1$-$C_8$-haloalkyl or

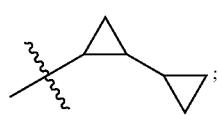 [SMILES: *C1CC1C1CC1]

;

$R^{2a}$, $R^{3a}$ and $R^{4a}$ are each independently $C_1$-$C_8$-alkyl or $C_1$-$C_8$-haloalkyl;
$Y^2$ and $Y^3$ are independently O, S, N;
$R^{2b}$ and $R^{3b}$ are independently $C_1$-$C_8$-alkyl, wherein $R^{2b}$ and $R^{3b}$ are optionally joined to form a 5-8 membered ring;
$R^{4b}$ and $R^{5b}$ are independently $C_1$-$C_8$-alkyl;
$R^{5a}$ is hydrogen or halogen.

6. A method according to claim 1, wherein step a) comprises dissolving the compound of formula III in solvent.

7. The method of claim 1, wherein the ligand is N,N' dimethyl 1,2 diamine cyclohexane, N,N' dimethyl 1,2 diethylamine, or N1-methyl-propane-1,3-diamine.

8. A method according to claim 1, wherein the reaction is performed in the presence of a base.

9. A method of preparing a compound of formula ID comprising performing the reaction represented by scheme 1D:

Scheme 1D

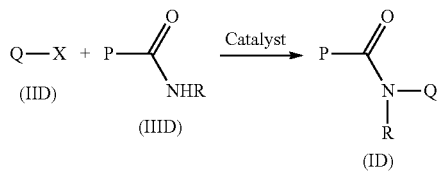

wherein Q is group V, group VI or group VIIa, group VIIb or group VIIc:

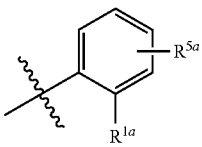

(V)

-continued

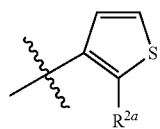
(VI)

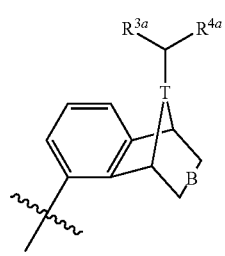
(VIIa)

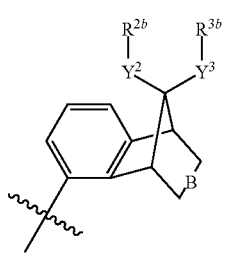
(VIIb)

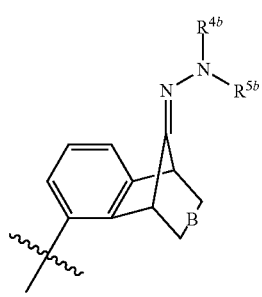
(VIIc)

B is a single or double bond;
T is a single or double bond;
$R^{1a}$ is phenyl optionally substituted with one to three halogen atoms, or $R^{1a}$ is $C_1$-$C_8$-alkyl, $C_1$-$C_8$-haloalkyl or

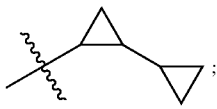 [SMILES: *C1CC1C1CC1]
;

$R^{2a}$, $R^{3a}$ and $R^{4a}$ are each independently $C_1$-$C_8$ alkyl or $C_1$-$C_8$ haloalkyl;
$Y^2$ and $Y^3$ are independently O, S, N;
$R^{2b}$ and $R^{3b}$ are independently $C_1$-$C_8$-alkyl, wherein $R^{2b}$ and $R^{3b}$ are optionally joined to form a 5-8 membered ring;
$R^{4b}$ and $R^{5b}$ are independently $C_1$-$C_8$-alkyl;
$R^{5a}$ is hydrogen or halogen;

X is chlorine;
R is hydrogen;
P is group VIII or group IX:

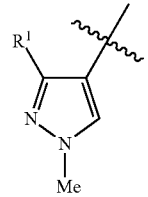
(VIII)

wherein $R^1$ is $CF_3$, $CHF_2$ or $CH_2F$;

(IX)

wherein $R^x$ is selected from $CF_3$, $CHF_2$ and $CH_3$;
wherein the catalyst comprises copper and a ligand;
wherein the ligand is an optionally substituted 1,2 diamine or an optionally substituted 1,3 diamine;
comprising the steps:
  a) providing the compound of formula IIID in liquid form,
  b) contacting the copper with the compound of formula IIID,
  c) contacting the ligand with the compound of formula IIID,
wherein at least one of steps b) and c) is performed after step a);
wherein step a) comprises heating the compound of formula IIID.

10. A method according to claim 1, wherein the reaction comprises preparing a compound of formula XXX:

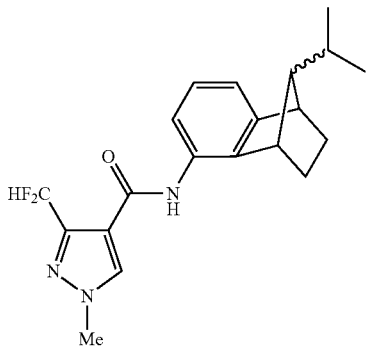
(XXX)

comprising the step of reacting a compound of formula XXXI:

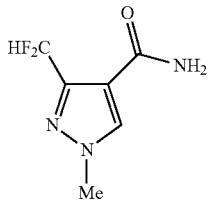
(XXXI)

with a compound of formula XXXII:

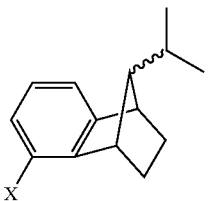
(XXXII)

wherein X is halogen or a sulphonate;

or wherein the reaction comprises preparing a compound of formula XXXV:

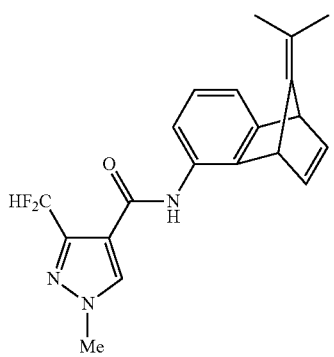
(XXXV)

comprising the step of reacting a compound of formula XXXI:

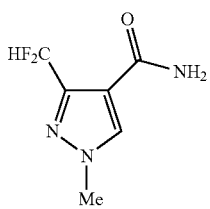
(XXXI)

with a compound of formula XXXVI:

(XXXVI)

wherein X is halogen or a sulphonate;

or wherein the reaction comprises preparing a compound of formula XXXVII:

(XXXVII)

comprising the step of reacting a compound of formula XXXI:

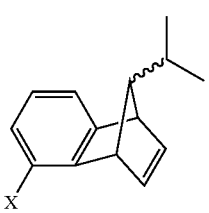
(XXXI)

with a compound of formula XXXIII (XXXIII)

wherein X is halogen or a sulphonate;

or
wherein the reaction comprises preparing a compound of formula XXXX:

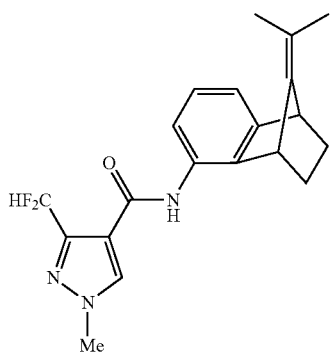

(XXXX)

comprising the step of reacting a compound of formula XXXI:

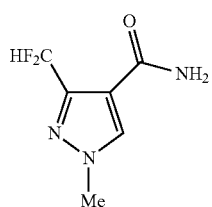

(XXXI)

with a compound of formula XXXXI:

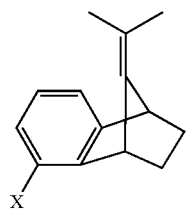

(XXXXI)

wherein X is halogen or a sulphonate;
or
wherein the reaction comprises preparing a compound of formula XXXXVII:

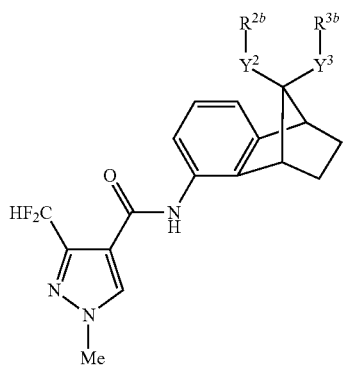

(XXXXVII)

wherein
$Y^2$ and $Y^3$ are independently O, S, N;
$R^{2b}$ and $R^{3b}$ are independently $C_1$-$C_8$-alkyl, wherein $R^{2b}$ and $R^{3b}$ are optionally joined to form a 5-8 membered ring;

comprising the step of reacting a compound of formula XXXXIV:

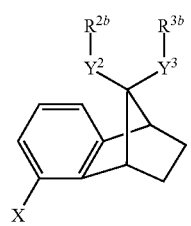

(XXXXIV)

wherein
$Y^2$, $Y^3$, $R^{2b}$ and $R^{3b}$ are as defined for formula XXXXVII;
X is halogen or a sulphonate;

with a compound of formula XXXI:

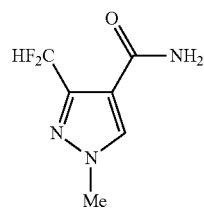

(XXXI)

or wherein the reaction comprises preparing a compound of formula XXXXVIII:

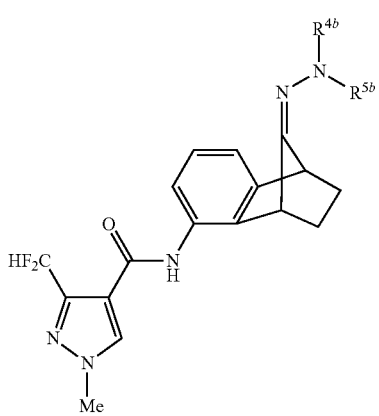

(XXXXVIII)

wherein
$R^{4b}$ and $R^{5b}$ are independently $C_1$-$C_8$-alkyl;

comprising the step of reacting a compound of formula XXXXV:

(XXXXV)

wherein
X is halogen or a sulphonate;
$R^{4b}$ and $R^{5b}$ are independently $C_1$-$C_8$-alkyl;
with a compound of formula XXXI:

(XXXI)

or
wherein the reaction comprises preparing a compound of formula XXXXIX:

(XXXXIX)

comprising the step of reacting a compound of formula XXXI:

(XXXI)

with a compound of formula L:

(L)

wherein X is halogen or a sulphonate;

or
wherein the reaction comprises preparing a compound of formula LI:

(LI)

comprising the step of reacting a compound of formula XXXI:

(XXXI)

with a compound of formula LII:

(LII)

wherein X is halogen or a sulphonate;

or
wherein the reaction comprises preparing a compound of formula LV:

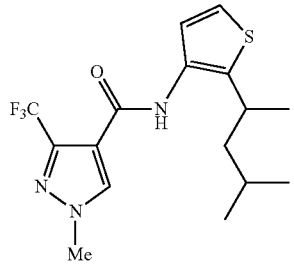
(LV)

comprising the step of reacting a compound of formula LVI:

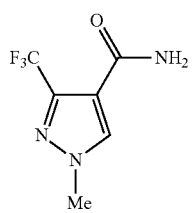
(LVI)

with a compound of formula LVII:

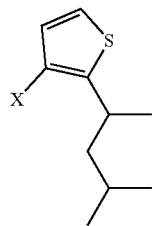
(LVII)

wherein X is halogen or a sulphonate;

or wherein the reaction comprises preparing a compound of formula LX:

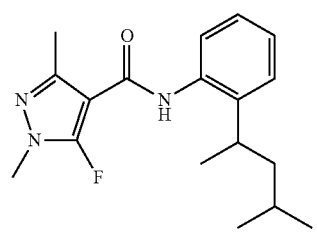
(LX)

comprising the step of reacting a compound of formula LXI:

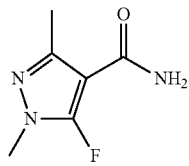
(LXI)

with a compound of formula LXII:

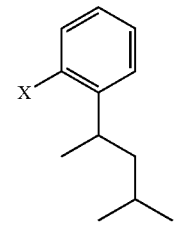
(LXII)

wherein X is halogen or a sulphonate;
or
or wherein the reaction comprises preparing a compound of formula LXV:

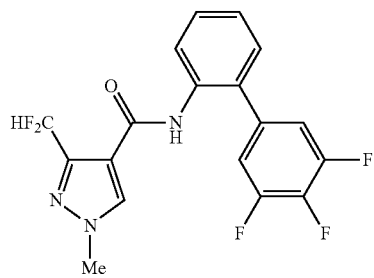
(LXV)

comprising the step of reacting a compound of formula XXXI:

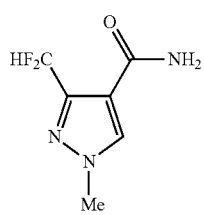
(XXXI)

with a compound of formula LXVI:

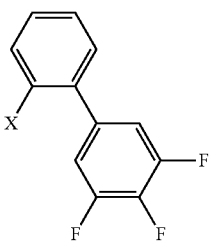
(LXVI)

wherein X is halogen or a sulphonate.

11. A method according to claim 1, wherein P is group VIII or group IX:

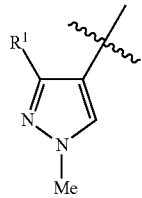
(VIII)

wherein $R^1$ is $CF_3$, $CHF_2$ or $CH_2F$;

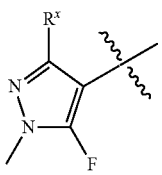
(IX)

wherein $R^x$ is selected from $CF_3$, $CHF_2$ and $CH_3$;

wherein Q is group V, group VI or group VIIa, group VIIb or group VIIc:

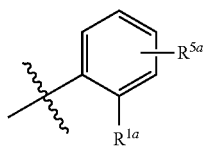
(V)

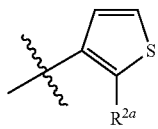
(VI)

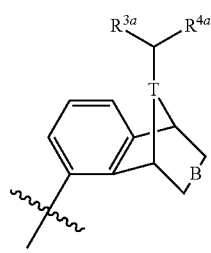
(VIIa)

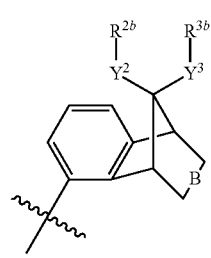
(VIIb)

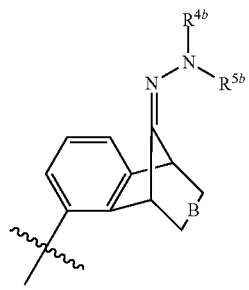
(VIIc)

B is a single or double bond;

T is a single or double bond;

$R^{1a}$ is phenyl optionally substituted with one to three halogen atoms, or $R^{1a}$ is $C_1$-$C_8$-alkyl, $C_1$-$C_8$-haloalkyl or

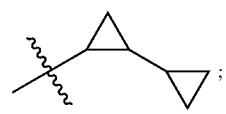
;

$R^{2a}$, $R^{3a}$ and $R^{4a}$ are each independently $C_1$-$C_8$-alkyl or $C_1$-$C_8$-haloalkyl;

$Y^2$ and $Y^3$ are independently O, S, N;

$R^{2b}$ and $R^{3b}$ are independently $C_1$-$C_8$-alkyl, wherein $R^{2b}$ and $R^{3b}$ are optionally joined to form a 5-8 membered ring;

$R^{4b}$ and $R^{5b}$ are independently $C_1$-$C_8$-alkyl;

$R^{5a}$ is hydrogen or halogen;

wherein R is hydrogen;

wherein X is halogen;

and wherein the ligand is an optionally substituted 1,2 diamine or an optionally substituted 1,3 diamine.

12. A method according to claim 2, wherein P is group VIII or group IX:

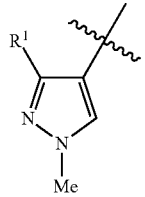
(VIII)

wherein $R^1$ is $CF_3$, $CHF_2$ or $CH_2F$;

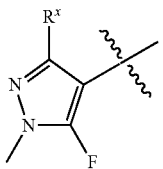
(IX)

wherein $R^x$ is selected from $CF_3$, $CHF_2$ and $CH_3$;

wherein Q is group V, group VI or group VIIa, group VIIb or group VIIc:

(V) 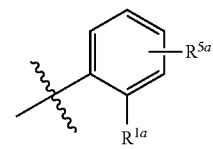

(VI) 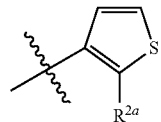

(VIIa) 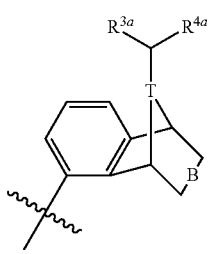

(VIIb) 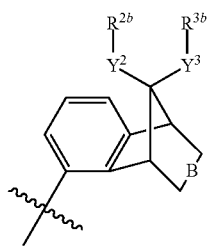

(VIIc) 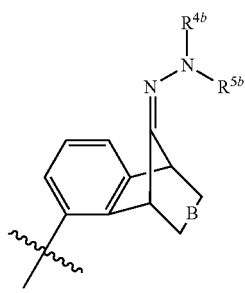

B is a single or double bond;
T is a single or double bond;
$R^{1a}$ is phenyl optionally substituted with one to three halogen atoms, or $R^{1a}$ is $C_1$-$C_8$-alkyl, $C_1$-$C_8$-haloalkyl or

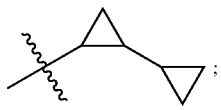

$R^{2a}$, $R^{3a}$ and $R^{4a}$ are each independently $C_1$-$C_8$-alkyl or $C_1$-$C_8$-haloalkyl;
$Y^2$ and $Y^3$ are independently O, S, N;
$R^{2b}$ and $R^{3b}$ are independently $C_1$-$C_8$-alkyl, wherein $R^{2b}$ and $R^{3b}$ are optionally joined to form a 5-8 membered ring;
$R^{4b}$ and $R^{5b}$ are independently $C_1$-$C_8$-alkyl;
$R^{5a}$ is hydrogen or halogen;
wherein R is hydrogen;
wherein X is halogen;
and wherein the ligand is an optionally substituted 1,2 diamine or an optionally substituted 1,3 diamine.

13. A method according to claim 2, wherein step a) comprises dissolving the compound of formula IIIA in solvent.

14. A method of claim 2, wherein the ligand is N,N' dimethyl 1,2 diamine cyclohexane, N,N' dimethyl 1,2 diethylamine, or N1-methyl-propane-1,3-diamine.

15. A method according to claim 2, wherein the reaction is performed in the presence of a base.

16. A method according to claim 2, wherein the compound of formula IIIA is a compound of formula XXII or LXIII:

(XXII) 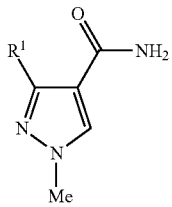

wherein $R^1$ is $CF_3$, $CHF_2$ or $CH_2F$;

(LXIII) 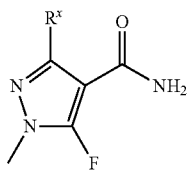

wherein $R^x$ is selected from $CF_3$, $CHF_2$ and $CH_3$.

* * * * *